United States Patent
Trauner et al.

(10) Patent No.: US 8,178,496 B2
(45) Date of Patent: May 15, 2012

(54) PHOTOREACTIVE REGULATOR OF GLUTAMATE RECEPTOR FUNCTION AND METHODS OF USE THEREOF

(75) Inventors: Dirk Trauner, San Francisco, CA (US); Ehud Y. Isacoff, Berkeley, CA (US); Matthew Volgraf, Oakland, CA (US); Pablo Ignacio Gorostiza Langa, Barcelona (ES)

(73) Assignee: The Regents of the University of California, Oakland, CA (US)

( * ) Notice: Subject to any disclaimer, the term of this patent is extended or adjusted under 35 U.S.C. 154(b) by 371 days.

(21) Appl. No.: 12/338,880

(22) Filed: Dec. 18, 2008

(65) Prior Publication Data

US 2009/0181454 A1 Jul. 16, 2009

Related U.S. Application Data

(60) Provisional application No. 61/016,233, filed on Dec. 21, 2007.

(51) Int. Cl.
*C07C 323/12* (2006.01)
*A61A 38/00* (2006.01)

(52) U.S. Cl. ....... 514/17.3; 514/17.4; 435/7.8; 435/334; 435/292.1

(58) Field of Classification Search .................. None
See application file for complete search history.

(56) References Cited

U.S. PATENT DOCUMENTS

2003/0017479 A1* 1/2003 Kaplan et al. .................. 435/6
2007/0128662 A1   6/2007 Isacoff et al.

OTHER PUBLICATIONS

University of Bristol (2010, Updated) "Glutamate Receptors", www.bristol.ac.uk/synaptic/receptors, pp. 1-3.*
Bacterial/prokaryotic Phylogeny (2010, updated) Archaea—How Are They Related to Other Prokaryotes, www.bacterialphylogeny.info/archaea.html, pp. 1-3.*
Katsuki et al. (2004) Endogenous D-Serine Is Involved in Induction of Neuronal Death by N-Methyl-D-aspartate and Simulated Ischemia in Rat Cerebrocortical Slices, J. . Pharmacol. Exp. Therap., vol. 311, pp. 836-844.*
Volgraf et al. (Jan. 2007) Reversibly caged glutamate: a photochromic agonist of ionotropic glutamate receptors, J. Am. Chem. Soc., vol. 129, pp. 260-261.*
Volgarf et al. (2006) Allosteric control of an ionotropic glutamate receptor with an optical switch, Nat. Chem. Biol., vol. 2, No. 1, pp. 47-52.*
Bulley et al. (2010) Reciprocal regulation between taurine and glutamate response via Ca2+-dependent pathways in retinal third-order neurons, J. Biomed. Sci., vol. 17, Suppl. S5, pp. 1-15.*
Chenu et al. (1998) Glutamate receptors are expressed by bone cells and are involved in bone resorption, Bone, vol. 22, No. 22, pp. 295-299.*
Wu et al. (2004) You have requested: Conformation of Azobenzene-Modified Poly($\alpha$-L-Glutamate) (AZOPLGA) in Thin Films: Solid State NMR Studies, J. MAcromol. Sci., vol. 41, No. 12, pp. 1259-1368.*
Zhang et al. (2006) Channelrhodopsin-2 and optical control of excitable cells, Nature Meth., Vo. 3, No. 10, pp. 786-792.*
Lindstrom et al. (1972) Study of frog sartorius muscle acetylcholine receptor using the irreversible inhibitor TDF, vol. 9, No. 1, pp. 155-176.*
Aemissegger et al. (Feb. 2007) Synthesis and application of an azobenzene amino acid as a light-switchable turn element in polypeptides, Nature Protocol, vol. 2, No. 12, pp. 161-1167.*
Dingledine et al. (1999) The Glutamate Receptor Ion Channels, Pharmacol. Rev., vol. 51, No. 1, pp. 7-61.*
Bartels, et al. Phototromic activators of the acetylcholine receptor. (1971) Proc. Natl. Acad. Sci. U.S.A. 68:1820-1823.
Banghart et al. Light-activated ion channels for remote control of neuronal firing. (2004) Nature Neurosci. 7, 1381-1386.
Caamano et al. A light-modulated sequence-specific DNA-binding peptide. (2000) Angew. Chem., Int. Ed. Engl. 39:3104-3107.
Fujita et al. Light control of mitochondrial complex I activity by a photoresponsive inhibitor. (2006) Biochemistry 45:6581-6586.
Givens et al. New photoprotecting groups: desyl and p-hydroxyphenacyl phosphate and carboxylate esters. (1998) In Methods in Enzymology, Marriott, G., Ed. Academic Press, New York, 291:1-29.
Kaufman et al. Photoregulation of an enzymic process by means of a light-sensitive ligand. (1968) Science 162:1487-1489.
Lester et al. J. Gen. Physiol. A covalently bound photoisomerizable agonist: comparison with reversibly bound agonists at Electrophorus electroplaques. (1980) 75, 207-232.
Mayer and Heckel. Biologically active molecules with a "light switch". (2006) Angew. Chem., Int. Ed. Engl. 45:4900-4921.
Volgraf et al. Allosteric control of an ionotropic glutamate receptor with an optical switch. (2006) Nature Chem. Biol. 2:47-52.
Ajit G. Thomas, et al., "Toxicity Induced by a Polyglutamated Folate Analog is Attenuated by NAALADase Inhibition", 1999, Brain Research, 843: 48-52.

* cited by examiner

*Primary Examiner* — Anand Desai
*Assistant Examiner* — Samuel Liu
(74) *Attorney, Agent, or Firm* — Paula A. Borden; Bozicevic, Field & Francis LLP.

(57) ABSTRACT

The present invention provides a synthetic regulator of glutamate receptor function, which regulator is a light-sensitive (photoreactive) regulator. The present invention further provides a light-regulated glutamate receptor that includes a subject synthetic regulator non-covalently associated with the glutamate receptor. Also provided are cells and membranes comprising a subject light-regulated glutamate receptor. The present invention further provides methods of modulating glutamate receptor function, involving use of light. The present invention further provides methods of identifying agents that modulate glutamate receptor function.

7 Claims, 6 Drawing Sheets

PHOTOREACTIVE REGULATOR OF GLUTAMATE RECEPTOR FUNCTION AND METHODS OF USE THEREOF

CROSS-REFERENCE

This application claims the benefit of U.S. Provisional Patent Application No. 61/016,233 filed Dec. 21, 2007, which application is incorporated herein by reference in its entirety.

STATEMENT REGARDING FEDERALLY SPONSORED RESEARCH

This invention was made with government support under Grant Number R01GM057027 awarded by the National Institutes of Health. The U.S. government has certain rights in the invention.

BACKGROUND

The ability to control the active concentration of neurotransmitters in a spatially and temporally precise manner has revolutionized the study of the central nervous system. In particular, caged glutamate has emerged as a tool for the dissection of both neural circuitry and the fast kinetic events of channel activation. Upon the irreversible photochemical cleavage of a protecting group, released glutamate is free to bind ionotropic glutamate receptors (iGluRs), the major mediators of excitatory information transfer in the central nervous system.

Photochromic ligands provide another opportunity for the control of neural excitability. First reported in the late 1960's in the form of a photoisomerizable inactivator of chymotrypsin, photochromic ligands control the function of proteins through a reversible change in shape and/or polarity of an integral bistable photoswitch. In the case of photochromic agonists, one configuration functions as an activating ligand, while the other configuration is, ideally, inert toward the system of study. Photochromic nicotinic acetylcholine receptor agonists, enzyme inhibitors, and regulatory peptides have been reported; however, their benefits have been tempered by the difficulty of achieving perfect on/off activity between states.

Literture

Kaufman et al. (1968) *Science* 162:1487-1489; Bartels et al. (1971) *Proc. Natl. Acad. Sci. U.S.A.* 68:1820-1823; Fujita et al. (2006) *Biochemistry* 45:6581-6586; Caamano et al. (2000) *Angew. Chem., Int. Ed. Engl.* 39:3104-3107; Mayer and Heckel (2006) *Angew. Chem., Int. Ed. Engl.* 45:4900-4921; Givens et al. (1998) In *Methods in Enzymology*, Marriott, G., Ed. Academic Press, New York, 291:1-29; Volgraf et al. (2006) *Nature Chem. Biol.* 2:47-52; U.S. Patent Publication No. 2007/0128662; Lester et al. *J. Gen. Physiol.* 75, 207-232 (1980); Banghart et al. *Nature Neurosci.* 7, 1381-1386 (2004).

SUMMARY OF THE INVENTION

The present invention provides a synthetic regulator of glutamate receptor function, which regulator is a light-sensitive (photoreactive) regulator. The present invention further provides a light-regulated glutamate receptor that includes a subject synthetic regulator non-covalently associated with the glutamate receptor. Also provided are cells and membranes comprising a subject light-regulated glutamate receptor. The present invention further provides methods of modulating glutamate receptor function, involving use of light. The present invention further provides methods of identifying agents that modulate glutamate receptor function.

DEFINITIONS

Figure 1:
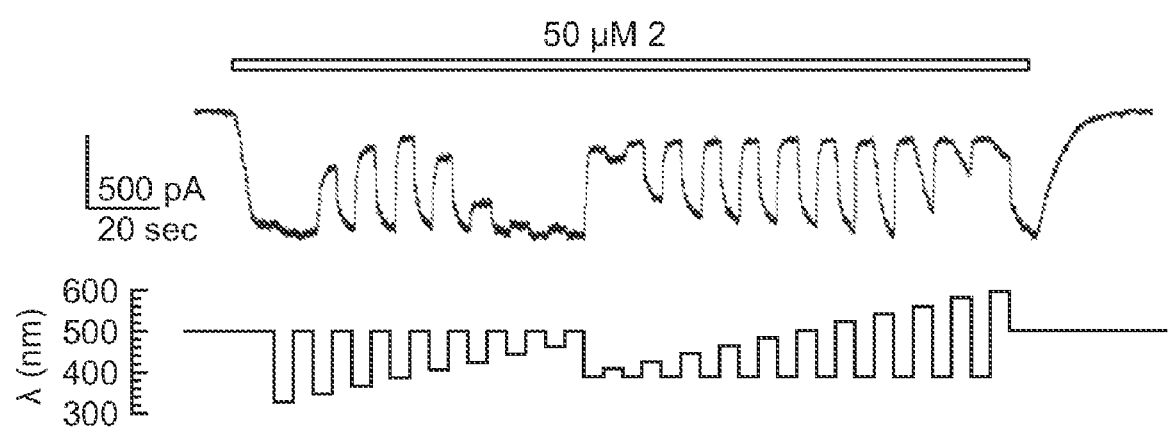
FIG. 1 depicts whole-cell voltage clamp recording of iGluR6(q) currents in HEK293 cells under UV-visible illumination.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. The term "polypeptide" includes polypeptides comprising one or more of a fatty acid moiety, a lipid moiety, a sugar moiety, and a carbohydrate moiety. The term "polypeptides" includes post-translationally modified polypeptides.

The term "naturally-occurring" as used herein as applied to a polypeptide, a cell, or an organism, refers to a polypeptide, cell, or organism that is found in nature. For example, a polypeptide having an amino acid sequence that is present in an organism (including viruses) that can be isolated from a source in nature and which has not been intentionally modified by a human in the laboratory is naturally occurring.

The term "determining" includes any form of measurement, and includes determining if an effect is present or not. The terms "determining", "measuring", "evaluating", "assessing" and "assaying" are used interchangeably and include quantitative and qualitative determinations. Assessing may be relative or absolute. "Determining the effect of" includes determining the degree of an effect, and/or determining whether any effect has occurred. As used herein, the terms "determining," "measuring," and "assessing," and "assaying" are used interchangeably and include both quantitative and qualitative determinations.

A "host cell," or "a cell," as used herein, denotes an in vivo or in vitro prokaryotic cell, an in vivo or in vitro eukaryotic cell, or a cell from a multicellular organism (e.g., a cell line) cultured in vitro as a unicellular entity. A cell includes a cell that comprises a subject light-regulated glutamate receptor. A "host cell" includes cells that can be, or have been, used as recipients for an exogenous nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, in some embodiments a subject host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, particularly humans. Non-human animal models, particularly mammals, e.g. non-human primates, murines, lagomorpha, etc. may be used for experimental investigations.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a synthetic regulator" includes a plurality of such regulators and reference to "the glutamate receptor" includes reference to one or more glutamate receptors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides a synthetic regulator of glutamate receptor function, which regulator is a light-sensitive (photoreactive) regulator. The present invention further provides a light-regulated glutamate receptor that includes a subject synthetic regulator non-covalently associated with the glutamate receptor. Also provided are cells and membranes comprising a subject light-regulated glutamate receptor. The present invention further provides methods of modulating glutamate receptor function, involving use of light. The present invention further provides methods of identifying agents that modulate glutamate receptor function.

Synthetic Regulator of Glutamate Receptor Function

The present invention provides a synthetic regulator of glutamate receptor function, which regulator is a light-sensitive (photoreactive) regulator. A subject synthetic protein regulator comprises: a) a photoisomerizable group; and b) a ligand that binds to a ligand binding site of a glutamate receptor. A subject synthetic regulator does not include a linker domain comprising a binding moiety that provides for stable association with a polypeptide such as a glutamate receptor. Instead, a subject synthetic regulator forms non-covalent associations with a glutamate receptor. A subject synthetic glutamate receptor regulator (also referred to as a "synthetic regulator," or "a photoswitch") associates non-covalently with a glutamate receptor.

A subject synthetic regulator can be provided in any number of configurations, including linear and branched. In some embodiments, a subject synthetic regulator has the structure: $(A)_m$-$(B)_p$, where A is a photoisomerizable group, and B is a ligand, and where each of m and p is independently 1 to 10, e.g., where each of m and p is independently one, two, three, four, five, six, seven, eight, nine, or ten. In some embodiments, each of m and p is 1, e.g., a subject synthetic regulator has the structure B-C. In other embodiments, a subject synthetic regulator comprises two or more (e.g., 2 to 10, e.g., two, three, four, five, six, seven, eight, nine, or ten) photoisomerizable groups. In some embodiments, where the synthetic regulator comprises two or more photoisomerizable groups, the two or more photoisomerizable groups are arranged in tandem, either directly or separated by a spacer. In some embodiments, a subject synthetic regulator comprises two or more different ligands.

In other embodiments, a subject synthetic regulator has the structure: B-$X_1$-A-$X_2$-B, where A is a photoisomerizable group, and B is a ligand, where $X_1$, when present, is a spacer, and where $X_2$, when present, is a spacer. Suitable spacers include peptide spacers (e.g., spacers of from about 1 to about 20 amino acids in length; non-peptide spacers, e.g., non-peptide polymers of various numbers of monomeric units, e.g., from one to about 20 units. In these embodiments, A (a photoisomerizable group) can be present in multiple copies, either directly or in tandem.

Photoisomerizable Group

The photoisomerizable group is one that changes from a first isomeric form to a second isomeric form upon exposure to light of different wavelengths, or upon a change in exposure from dark to light, or from light to dark. For example, in some embodiments, the photoisomerizable group is in a first isomeric form when exposed to light of a first wavelength, and is in a second isomeric form when exposed to light of a second wavelength. Suitable photoisomerizable groups include stereoisomers and constitutional isomers.

The first wavelength and the second wavelength can differ from one another by from about 1 nm to about 2000 nm or more, e.g., from about 1 nm to about 10 nm, from about 10 nm to about 20 nm, from about 20 nm to about 50 nm, from about 50 nm to about 75 nm, from about 75 nm to about 100 nm, from about 100 nm to about 125 nm, from about 125 nm to about 150 nm, or from about 150 nm to about 200 nm, from about 200 nm to about 500 nm, from about 500 nm to about 800 nm, from about 800 nm to about 1000 nm, from about 1000 nm to about 1500 nm, from about 1500 nm to about 2000 nm, or more than 2000 nm.

In other embodiments, the photoisomerizable group is in a first isomeric form when exposed to light of a wavelength $\lambda_1$, and is in a second isomeric form in the absence of light (e.g., in the absence of light, the photoisomerizable group undergoes spontaneous relaxation into the second isomeric form). In these embodiments, the first isomeric form is induced by exposure to light of wavelength $\lambda_1$, and the second isomeric form is induced by not exposing the photoisomerizable group to light, e.g., keeping the photoisomerizable group in darkness. In other embodiments, the photoisomerizable group is in a first isomeric form in the absence of light, e.g., when the photoisomerizable group is in the dark; and the photoisomerizable group is in a second isomeric form when exposed to light of a wavelength $\lambda_1$. In other embodiments, the photoisomerizable group is in a first isomeric form when exposed to light of a first wavelength $\lambda_1$, and the photoisomerizable group is in a second isomeric form when exposed to light of second wavelength $\lambda_2$.

For example, in some embodiments, the photoisomerizable group is in a trans configuration in the absence of light, or when exposed to light of a first wavelength; and the photoisomerizable group is in a cis configuration when exposed to light, or when exposed to light of a second wavelength that is different from the first wavelength. As another example, in some embodiments, the photoisomerizable group is in a cis configuration in the absence of light, or when exposed to light of a first wavelength; and the photoisomerizable group is in a trans configuration when exposed to light, or when exposed to light of a second wavelength that is different from the first wavelength.

The wavelength of light that effects a change from a first isomeric form to a second isomeric form ranges from $10^{-8}$ m to about 1 m, e.g., from about $10^{-8}$ m to about $10^{-7}$ m, from about $10^{-7}$ m to about $10^{-6}$ m, from about $10^{-6}$ m to about $10^{-4}$ m, from about $10^{-4}$ m to about $10^{-2}$ m, or from about $10^{-2}$ m to about 1 m. "Light," as used herein, refers to electromagnetic radiation, including, but not limited to, ultraviolet light, visible light, infrared, and microwave.

The wavelength of light that effects a change from a first isomeric form to a second isomeric form ranges in some embodiments from about 200 nm to about 800 nm, e.g., from about 200 nm to about 250 nm, from about 250 nm to about 300 nm, from about 300 nm to about 350 nm, from about 350 nm to about 400 nm, from about 400 nm to about 450 nm, from about 450 nm to about 500 nm, from about 500 nm to about 550 nm, from about 550 nm to about 600 nm, from about 600 nm to about 650 nm, from about 650 nm to about 700 nm, from about 700 nm to about 750 nm, or from about 750 nm to about 800 nm, or greater than 800 nm.

In other embodiments, the wavelength of light that effects a change from a first isomeric form to a second isomeric form ranges from about 800 nm to about 2500 nm, e.g., from about 800 nm to about 900 nm, from about 900 nm to about 1000 nm, from about 1000 nm to about 1200 nm, from about 1200 nm to about 1400 nm, from about 1400 nm to about 1600 nm, from about 1600 nm to about 1800 nm, from about 1800 nm to about 2000 nm, from about 2000 nm to about 2250 nm, or from about 2250 nm to about 2500 nm. In other embodiments, the wavelength of light that effects a change from a first isomeric form to a second isomeric form ranges from about 2 nm to about 200 nm, e.g., from about 2 nm to about 5 nm, from about 5 nm to about 10 nm, from about 10 nm to about 25 nm, from about 25 nm to about 50 nm, from about 50 nm to about 75 nm, from about 100 nm, from about 100 nm to about 150 nm, or from about 150 nm to about 200 nm.

The difference between the first wavelength and the second wavelength can range from about 1 nm to about 2000 nm or more, as described above. Of course, where the synthetic light regulator is switched from darkness to light, the difference in wavelength is from essentially zero to a second wavelength.

The intensity of the light can vary from about 1 $W/m^2$ to about 50 $W/m^2$, e.g., from about 1 $W/m^2$ to about 5 $W/m^2$, from about 5 $W/m^2$ to about 10 $W/m^2$, from about 10 $W/m^2$, from about 10 $W/m^2$ to about 15 $W/m^2$, from about 15 $W/m^2$ to about 20 $W/m^2$, from about 20 $W/m^2$ to about 30 $W/m^2$, from about 30 $W/m^2$ to about 40 $W/m^2$, or from about 40 $W/m^2$ to about 50 $W/m^2$. The intensity of the light can vary from about 1 $\mu W/cm^2$ to about 100 $\mu W/cm^2$, e.g., from about 1 $\mu W/cm^2$ to about 5 $\mu W/cm^2$, from about 5 $\mu W/cm^2$ to about 10 $\mu W/cm^2$, from about 10 $\mu W/cm^2$ to about 20 $\mu W/cm^2$, from about 20 $\mu W/cm^2$ to about 25 $\mu W/cm^2$, from about 25 $\mu W/cm^2$ to about 50 $\mu W/cm^2$, from about 50 $\mu W/cm^2$ to about 75 $\mu W/cm^2$, or from about 75 $\mu W/cm^2$ to about 100 $\mu W/cm^2$. In some embodiments, the intensity of light varies from about 1 $\mu W/mm^2$ to about 1 $\mu W/mm^2$, e.g., from about 1 $\mu W/mm^2$ to about 50 $\mu W/mm^2$, from about 50 $\mu W/mm^2$ to about 100 $\mu W/mm^2$, from about 100 $\mu W/mm^2$ to about 500 $\mu W/mm^2$, from about 500 $\mu W/mm^2$ to about 1 $mW/mm^2$, from about 1 $mW/mm^2$ to about 250 $mW/mm^2$, from about 250 $mW/mm^2$ to about 500 $mW/mm^2$, or from about 500 $mW/mm^2$ to about 1 $\mu W/mm^2$.

In some embodiments, the change from a first isomeric form to a second isomeric form of the photoisomerizable group is effected using sound, instead of electromagnetic (EM) radiation (light). For example, in some embodiments, the change from a first isomeric form to a second isomeric form of the photoisomerizable group is effected using ultrasound.

Photoisomerizable groups are known in the art, and any known photoisomerizable group can be included in a subject synthetic regulator of protein function. Suitable photoisomerizable groups include, but are not limited to, azobenzene and derivatives thereof; spiropyran and derivatives thereof; triphenyl methane and derivatives thereof; 4,5-epoxy-2-cyclopentene and derivatives thereof; fulgide and derivatives thereof; thioindigo and derivatives thereof; diarylethene and derivatives thereof; diallylethene and derivatives thereof; overcrowded alkenes and derivatives thereof; and anthracene and derivatives thereof. In some embodiments, a suitable photoisomerizable group is a photoisomerizable group as shown in the Example.

Suitable spiropyran derivatives include, but are not limited to, 1,3,3-trimethylindolinobenzopyrylospiran; 1,3,3-trimethylindolino-6'-nitrobenzopyrylospiran; 1,3,3-trimethylindolino-6'-bromobenzopyrylospiran; 1-n-decyl-3,3-dimethylindolino-6'-nitrobenzopyrylospiran; 1-n-octadecy-1-3,3-dimethylindolino-6'-nitrobenzopyrylospiran; 3',3'-dimethyl-6-nitro-1'-[2-(phenylcarbamoyl)ethyl]spiro; [2H-1-benzopyran-2,2'-indoline]; 1,3,3-trimethylindolino-8'-methoxybenzopyrylospiran; and 1,3,3-trimethylindolino-β-naphthopyrylospiran. Also suitable for use is a merocyanine form corresponding to spiropyran or a spiropyran derivative.

Suitable triphenylmethane derivatives include, but are not limited to, malachite green derivatives. specifically, there can be mentioned, for example, bis[dimethylamino)phenyl]phenylmethanol, bis[4-(diethylamino)phenyl]phenylmethanol, bis[4-(dibutylamino)phenyl]phenylmethanol and bis[4-(diethylamino)phenyl]phenylmethane.

Suitable 4,5-epoxy-2-cyclopentene derivatives include, for example, 2,3-diphenyl-1-indenone oxide and 2',3'-dimethyl-2,3-diphenyl-1-indenone oxide.

Suitable azobenzene compounds include, e.g., compounds having azobenzene residues crosslinked to a side chain, e.g., compounds in which 4-carboxyazobenzene is ester bonded to the hydroxyl group of polyvinyl alcohol or 4-carboxyazobenzene is amide bonded to the amino group of polyallylamine. Also suitable are azobenzene compounds having azobenzene residues in the main chain, for example, those formed by ester bonding bis(4-hydroxyphenyl)dimethylmethane (also referred to as bisphenol A) and 4,4'-dicarboxyazobenzene or by ester bonding ethylene glycol and 4,4'-dicarboxyazobenzene.

Suitable fulgide derivatives include, but are not limited to, isopropylidene fulgide and adamantylidene fulgide.

Suitable diallylethene derivatives include, for example, 1,2-dicyano-1,2-bis(2,3,5-trimethyl-4-thienyl)ethane; 2,3-bis(2,3,5-trimethyl-4-thiethyl)maleic anhydride; 1,2-dicyano-1,2-bis(2,3,5-trimethyl-4-selenyl)ethane; 2,3-bis(2,3,5-trimethyl-4-selenyl)maleic anhydride; and 1,2-dicyano-1,2-bis(2-methyl-3-N-methylindole)ethane.

Suitable diarylethene derivatives include but are not limited to, substituted perfluorocylopentene-bis-3-thienyls and bis-3-thienylmaleimides.

Suitable overcrowded alkenes include, but are not limited to, cis-2-nitro-7-(dimethylamino)-9-(2',3'-dihydro-1'H-naphtho[2,1-b]thiopyran-1'-ylidene)-9H-thioxanthene and trans-dimethyl-[1-(2-nitro-thioxanthen-9-ylidene)-2,3-dihydro-1H-benzo[f]thiochromen-8-yl]amine. Overcrowded alkenes are described in the literature. See, e.g., terWiel et al. (2005) *Org. Biomol. Chem.* 3:28-30; and Geertsema et al. (1999) *Agnew CHem. Int. Ed. Engl.* 38:2738.

Other suitable photoisomerizable moieties include, e.g., reactive groups commonly used in affinity labeling, including diazoketones, aryl azides, diazerenes, and benzophenones.

Glutamate Receptors

A glutamate receptor is a protein (or a multi-subunit protein complex) that, upon binding glutamate, is activated. Two main categories of glutamate receptors have been identified, ionotropic and metabotropic. Ionotropic glutamate receptors (iGluR) can be subdivided into N-methyl-D-aspartate (NMDA) receptors (NMDA-R), α-amino-3-hydroxy-5-methyl-4-isoxazole-propionate (AMPA) receptors (AMPA-R), and kainate (KA) receptors (KA-R); this classification is based on preferential binding of a receptor to NMDA, AMPA, or KA. NMDA-R, AMPA-R, and KA-R have different subunit structures. The ionotropic glutamate receptors (iGluRs) are ligand-gated ion channels that, upon binding glutamate, open to allow the selective influx of certain monovalent and divalent cations, thereby depolarizing the cell membrane. In addition, certain iGluRs with relatively high calcium permeability can activate a variety of calcium-dependent intracellular processes. These receptors are multisubunit protein complexes that may be homomeric or heteromeric in nature. The various iGluR subunits all share common structural motifs, including a relatively large amino-terminal extracellular domain (ECD), followed by two transmembrane domains (TMD), a second smaller extracellular domain, and a third TMD, before terminating with an intracellular carboxy-terminal domain. The term "glutamate receptor" includes NMDA-R, KA-R, AMPA-R, mGluR, and taste receptors.

Metabotropic glutamate receptors (mGluR) can be subdivided into three classes, mGluRI, mGluRII and mGluRIII; this classification is based on amino acid sequence similarity, pharmacology, and intracellular signaling mechanism. mGluRs are G-protein-coupled receptors capable of activating a variety of intracellular second messenger systems following the binding of glutamate. Activation of mGluRs in intact mammalian neurons can elicit one or more of the following responses: activation of phospholipase C, increases in phosphoinositide (PI) hydrolysis, intracellular calcium release, activation of phospholipase D, activation or inhibition of adenylyl cyclase, increases or decreases in the formation of cyclic adenosine monophosphate (cAMP), activation of guanylyl cyclase, increases in the formation of cyclic guanosine monophosphate (cGMP), activation of phospholipase $A_2$, increases in arachidonic acid release, and increases or decreases in the activity of ion channels (e.g., voltage- and ligand-gated ion channels). Group I mGluRs comprise mGluR1, mGluR5, and their alternatively spliced variants. Group II mGluRs include mGluR2 and mGluR3. Group III mGluRs include mGluR4, mGluR6, mGluR7 and mGluR8.

Figure 2:
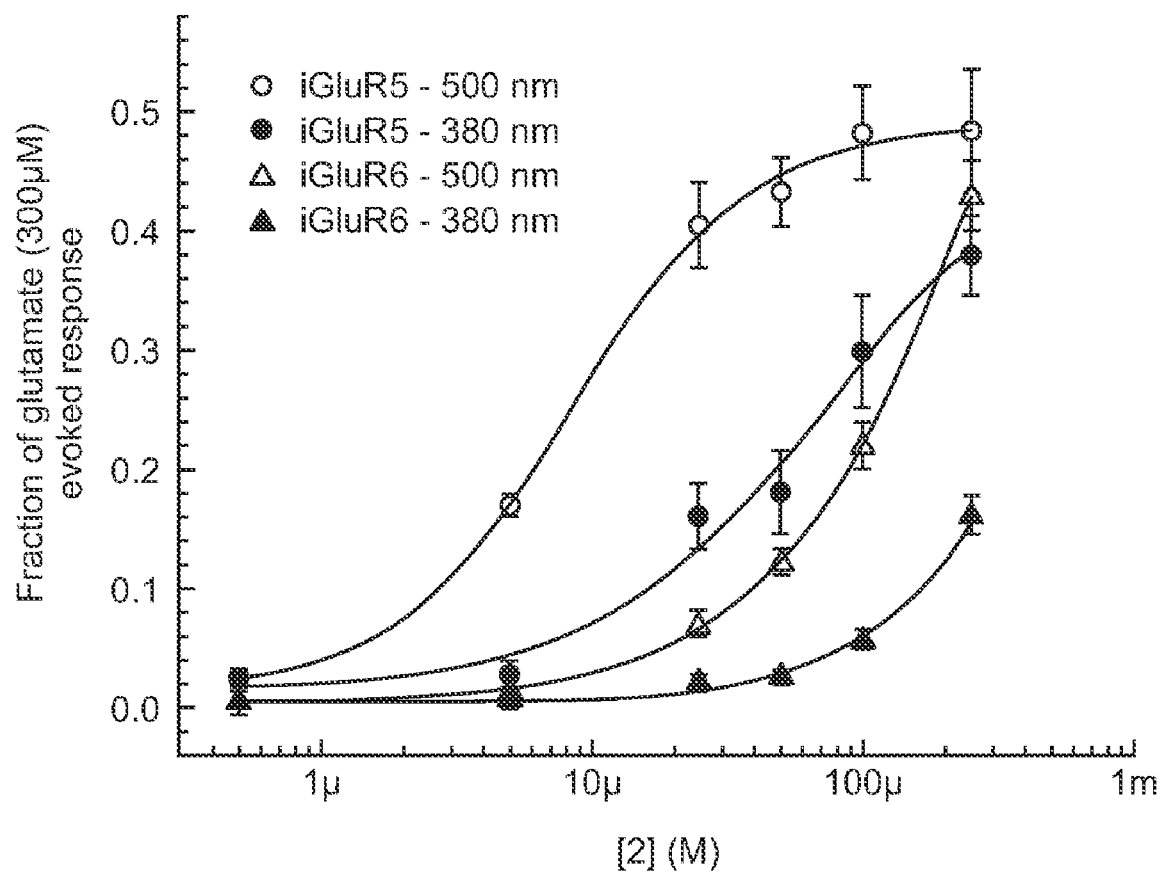
FIG. 2 depicts dose-response curves for inward currents evoked by 2 at iGluR5- and iGluR6-expressing HIK293 cells under 380 nm and 500 nm illumination.

Amino acid sequences of glutamate receptors are known in the art. See, e.g., the web site on the internet at www(dot)iuphar-db(dot)org. For example, amino acid sequences of the human Group III mGluRs mGluR4, mGluR7, and mGluR8 are described in, e.g., Wu et al. (1998) Brain Res. Mol. Brain. Res. 53:88-97. Amino acid sequences of several glutamate receptors are shown in FIG. 2 of Sutcliffe et al. ((1996) Biophys. J. 70:1575-1589), including KA1, KA2, and GluR1-7. mGluR1 amino acid sequences include, e.g., amino acid sequences provided in GenBank Accession Nos. Q13255 (human mGluR1); P23385 (rat mGlu R1); and P97772 (mouse mGluR1). mGluR2 amino acid sequence include, e.g., amino acid sequences provided in GenBank Accession Nos. Q14416 (human mGluR2); and P31421 (rat mGluR2). mGluR3 amino acid sequence include, e.g., amino acid sequences provided in GenBank Accession Nos. Q14832 (human mGluR3); P31422 (rat mGluR3); and Q9QYS2 (mouse mGluR3). mGluR4 amino acid sequence include, e.g., amino acid sequences provided in GenBank Accession Nos. Q14833 (human mGluR4); P31423 (rat mGluR4); and Q68EF4 (mouse mGluR4). mGluR5 amino acid sequence include, e.g., amino acid sequences provided in GenBank Accession Nos. P41594 (human mGluR5); and P31424 (rat mGluR5). mGluR6 amino acid sequence include, e.g., amino acid sequences provided in GenBank Accession Nos. O15303 (human mGluR6); P35349 (rat mGluR6); and Q5NCH9 (mouse mGluR6). See also GenBank Accession Nos. 1SD3_a and 1SD3_B. See also, e.g., GenBank Accession Nos. P42261, P42263, P42262, P48058, NP_068775, NP_786944, NP_000822, P39086, and Q13002. See also, e.g., Hoo et al. (1994) Recept. Channels 2:327; Sun et al. (1992) Proc. Natl. Acad. Sci. USA 89:1443; Potier et al. (1992) DNA Seq. 2:211; Puckett et al. (1991) Proc. Natl. Acad. Sci. USA 88:7557; Gregor et al. (1993) Neuroreport 4:1343; and Korczak et al. (1995) Recept. Channels 3:41.

In some embodiments, a suitable glutamate receptor is a taste receptor. See, e.g., U.S. Pat. No. 7,241,880. For example, in some embodiments, a taste receptor has an amino acid sequence that is at least 60%, at least 65%, at least 70%, at least 75%, at least 80%, at least 85%, at least 90%, at least 95%, at least 98%, or 100%, identical to the amino acid sequence of SEQ ID NO:21 of U.S. Pat. No. 7,241,880. See also Xu et al. (2004) Proc. Natl. Acad. Sci. USA 101:14258. In some embodiments, a taste receptor is a member of the T1R family of taste-cell-specific GPCRs. Members of the T1R family of taste-cell-specific GPCRs are identified in Hoon et al., Cell, 96:541 551 (1999), WO 00/06592, and WO 00/06593.

Modulating metabotropic glutamate receptor activity causes an increase or decrease in a cellular response which occurs upon metabotropic glutamate receptor activation. Cellular responses to metabotropic glutamate receptor activation vary depending upon the type of metabotropic glutamate receptor activated. Generally, metabotropic glutamate receptor activation causes one or more of the following activities: (1) activation of phospholipase C, (2) increases in phosphoinositide (PI) hydrolysis, (3) intracellular calcium release, (4) activation of phospholipase D, (5) activation or inhibition of adenylyl cyclase, (6) increases or decreases in the formation of cyclic adenosine monophosphate (cAMP), (7) activation of guanylyl cyclase, (8) increases in the formation of cyclic guanosine monophosphate (cGMP), (9) activation of phospholipase $A_2$, (10) increases in arachidonic acid release, and (11) increases or decreases in the activity of ion channels, for example voltage- and ligand-gated ion channels. Inhibition of metabotropic glutamate receptor activation reduces or prevents one or more of these activities from occurring.

Also suitable is the ligand-binding domain of any of the aforementioned glutamate receptors. Also suitable is a polypeptide comprising the ligand-binding domain of a glutamate receptor, fused to a heterologous protein. In some embodiments, a suitable glutamate receptor is an isolated ligand-binding domain of glutamate receptor, e.g., lacking any other domains that may be present in the native glutamate receptor.

In some embodiments, the glutamate receptor is a wild-type glutamate receptor, e.g., the glutamate receptor has a wild-type or natives amino acid sequence, e.g., an amino acid sequence that has not been altered by recombinant methods. In other embodiments, the glutamate receptor is a recombinant glutamate receptor. In some embodiments, the glutamate receptor is a synthetic glutamate receptor. Recombinant glutamate receptors include variant glutamate receptor that have been engineered such that the amino acid sequence differs from a wild-type or naturally-occurring glutamate receptor. Variant glutamate receptors include glutamate receptor comprising an amino acid sequence that differs from the amino acid sequence of a corresponding wild-type or naturally-occurring glutamate receptor by one to 15 amino acids.

In some embodiments, the glutamate receptor comprises one or more amino acid substitutions and/or insertions and/or deletions compared to the amino acid sequence of a naturally-occurring glutamate receptor.

In some embodiments, the glutamate receptor is a fusion protein, where the fusion protein includes a glutamate receptor fused in-frame to a heterologous protein, e.g., a protein other than a glutamate receptor, where the heterologous protein is also referred to as a "fusion partner." In some embodiments, the fusion partner is linked to the glutamate receptor at the N-terminus of the glutamate receptor. In other embodiments, the fusion partner is linked at the C-terminus of the glutamate receptor. In other embodiments, the fusion partner is internal to the glutamate receptor.

Suitable fusion partners include, but are not limited to, epitope tags; solubilization domains; polypeptides that provide for insertion into a biological membrane; polypeptides that provide for uptake into a cell, e.g., polypeptides that provide for uptake into the cytoplasm or into an intracellular compartment; polypeptides that selectively bind to native proteins, including at essential protein interaction interfaces; polypeptides that provide for subcellular localization; polypeptides that provide a detectable signal (e.g., fluorescent proteins; chromogenic proteins; enzymes that generate luminescent, fluorescent, or chromogenic products; and the like).

Suitable fusion partners include, but are not limited to, luciferase (e.g., firefly luciferase and derivatives thereof; *Renilla* luciferase and derivatives thereof); β-galactosidase; chloramphenicol acetyl transferase; glutathione S transferase; a green fluorescent protein (GFP), including, but not limited to, a GFP derived from *Aequoria victoria* or a derivative thereof, a number of which are commercially available; a GFP from a species such as *Renilla reniformis, Renilla mullei*, or *Ptilosarcus guernyi*, as described in, e.g., WO 99/49019 and Peelle et al. (2001) *J. Protein Chem.* 20:507-519; any of a variety of fluorescent and colored proteins from *Anthozoan* species, as described in, e.g., Matz et al. (1999) *Nature Biotechnol.* 17:969-973, U.S. Patent Publication No. 2002/0197676, or U.S. Patent Publication No. 2005/0032085; a red fluorescent protein; a yellow fluorescent protein (YFP), e.g., an enhanced YFP; a Lumio™ tag (e.g., a peptide of the sequence Cys-Cys-Xaa-Xaa-Cys-Cys, where Xaa is any amino acid other than cysteine, e.g., where Xaa-Xaa is Pro-Gly, which peptide is specifically bound by a fluorescein derivative having two As(III) substituents, e.g., 4',5'-bis(1,3,2-dithioarsolan-2-yl)fluorescein; see, e.g., Griffin et al. (1998) *Science* 281:269; Griffin et al. (2000) *Methods Enzymol.* 327:565; and Adams et al. (2002) *J. Am. Chem. Soc.* 124:6063); and the like.

Glutamate Receptor Ligands

As used herein, the term "ligand" refers to a molecule (e.g., a small molecule, a peptide, or a protein) that binds to a glutamate receptor and effects a change in an activity of the glutamate receptor, and/or effects a change in conformation of the glutamate receptor, and/or affects binding of another glutamate receptor to the glutamate receptor. Ligands include agonists, partial agonists, inverse agonists, antagonists, allosteric modulators, and blockers.

In some embodiments, the ligand is a naturally-occurring ligand. In other embodiments, the ligand is a synthetic ligand. In other embodiments, the ligand is an endogenous ligand. In some embodiments, the ligand is an agonist. In other embodiments, the ligand is an inverse agonist. In other embodiments, the ligand is a partial agonist. In other embodiments, the ligand is an antagonist. In other embodiments, the ligand is an allosteric modulator. In other embodiments, the ligand is a blocker. The term "antagonist" generally refers to an agent that binds to a glutamate receptor and inhibits an activity of the glutamate receptor. An "antagonist" may be an agent that binds to an allosteric site but does not activate the glutamate receptor; instead, the antagonist generally excludes binding by an agonist and thus prevents or hinders activation. The term "blocker" refers to an agent that acts directly on the active site, pore, or allosteric site. Ligands suitable for use herein bind reversibly to a ligand-binding site of a glutamate receptor. In some embodiments, the ligand is a reversibly caged ligand of a glutamate receptor.

In some embodiments, a ligand is a small molecule ligand. Small molecule ligands generally have a molecular weight in a range of from about 50 daltons to about 3000 daltons, e.g., from about 50 daltons to about 75 daltons, from about 75 daltons to about 100 daltons, from about 100 daltons to about 250 daltons, from about 250 daltons to about 500 daltons, from about 500 daltons to about 750 daltons, from about 750 daltons to about 1000 daltons, from about 1000 daltons to about 1250 daltons, from about 1250 daltons to about 1500 daltons, from about 1500 daltons to about 2000 daltons, from about 2000 daltons to about 2500 daltons, or from about 2500 daltons to about 3000 daltons.

NMDA-R Agonists

NMDA-R agonists include, e.g., N-Methyl-D-aspartate, glutamate, glycine, D-serine, homoquinolinic acid, and taurine.

NMDA-R Antagonists

NMDA-R antagonists refer to compounds that bind to NMDA receptors in a competitive manner or interact with NMDA receptor associated sites and block NMDA mediated signal in a non-competitive manner.

NMDA-R antagonists include L-glutamate derivatives, tetrahydroquinolines, imidazoloquinoxalinones, isatines, fused cycloalkylquinoxalinediones, quinoxalines, spermine, 4-hydroxy-3-nitro-1,2-dihydroquinolon-2-one derivatives, indole derivatives, benzo-thiadiazine dioxide derivatives, indeno(1,2-b)pyrazin-3-ones or corresponding 2,3-diones, quinoline derivatives, ethyl(phenyl-carbamoyl)-ethenyl)dichloroindole carboxylates, thienopyrazine 2,3-dione derivatives, 2-(2,3-dicarboxycyclopropyl)glycine, 2-amino-3-substituted phenyl propionic acid derivatives, 1-carboxyalkylquinoxaline-2.3(1H,4H)dione derivatives, thienyl-glycine derivatives, benzo-fused azacyclic compounds, tricyclic quinoxaline-diene derivatives, 3-hydroxy anthranilic acid and salts, decahydroisoquinolines, tri- or terta-substituted guanidine derivatives, D- or L-tryptophan derivatives, tetrazolyl(alkyl)-cyclohexyl-amino acid derivatives, octahydrophenanthrene derivatives, benzomorphan, piperazinyl or piperidinyl-alkyl substituted isoxazole derivatives, decahydroisoquinoline-3-carboxylic ester or its amide preparation, compounds based on Conantokin-G peptide, 3-heterocyclyl-alkyl-benzopyran-2-one derivatives, phosphono-alkyl imidazo-pyrimidine carboxylic acid derivatives, amantadine, memantine, rimantidine, histogranin and analogues, nitrobenzoic acid derivatives, e.g 4-((2-methoxycarbonyl-4-nitrophenyl)methyl)piperazine carboxylic acid, diamine derivatives with selective sigma receptor affinity, remacemide (2-amino-N-(1,2-diphenyl-1-methylethyl)acetamide), phosphono-alkylidene- or phosphono-alkoxy-imino-piperidine acid, benzothiadiazine carboxylic acid derivatives, dihydro-benzothiadiazine dioxide carboxylic acid derivatives, 4-hydroxy 2(H) pyrrolone derivatives, quinoxaline derivatives, tetrahydro-imidazo(1,2-a)pyrimidines or their salts, 4-hydroxy-pyrrolo(1,2-b)pyridazin-2(1H)-one derivatives, nitroquinolone derivatives, 3-aryl-substituted 2(1H)quinolone, 2(1H)-quinolone, phosphonic acid quinoline-2-carboxylic acid derivatives, benzimidazole(s) carrying 2 acidic groups, N,N'-disubstituted guanidine derivatives, tricyclic quinoxalinediones, 2-(2,3-dicarboxycyclopropyl)glycine, isatine derivatives, 3-amino-indolyl-derivatives, 2-phenyl-1,3-propanediol dicarbamate (felbamate), benzomorphan derivatives, dihydrothienopyridine derivatives, (aminophenyl)-heteroaryl ethylamine, pyridazinedione derivatives, a 2H-1-benzopyran-2-one compound, a 4-sulphonylaminoquinoline derivative, R(+)-3-amino-1-hydroxy-pyrrolidine-2-one, 2-carboxy indole, substituted. imino-methano dibenzo (A,D)cycloheptene derivatives, indole-hydrazone, piperazine derivatives, 4,6-disubstituted tryptophan and kynurenine derivatives, fluorenamine, diketo-pyridopyrazine derivatives or its salts, 2-amino-3,4-dioxo-1-cyclobutene derivatives, 2-acyl-amido derivatives of 3,4-dihydro-3-oxoquinoxaline, benzimidazole phosphono-amino acid derivatives, quinoxaline phosphono-amino acid derivatives, piperazine, piperidine or pyrrolidone derivatives, its salts and isomeric forms including stereoisomers, 4-hydroxy-2(1H)-quinolinone derivatives, its salts and prodrugs, fused pyrazine derivatives, 2-phenyl or 2-thienyl-(2)-piperidine derivatives, 3-amido or 3-sulphamido-indolyl derivatives, 3-aryl-4-hydroxy-2-(1H)-quinolone derivatives, 2-heterocyclyl-2-hydroxy-ethylamine derivatives, 1-aryl-2-aminomethyl pyrrolidine, its optical isomers and acid-addition salts, 4,6-dihalo indole-2-carboxylic acid derivatives, cyclic amino-hydroxamate derivatives, tetracyclic amine derivatives, 2,4-dioxo-1,2,3,4-tetrahydroquinoline derivatives, 2,4-dioxo-1,2,3,4-tetrahydroquinoline derivatives, 3-phosphonopiperidine and p-pyrrolidine derivatives, benzothieno(2,3-B)-pyrazine-2,3-(1H,4H)-dione, spiro dibenzosuberane derivatives, benzomorphan derivatives, preparation of 3,4-disubstituted 2-isoxazoline(s) and isoxazoles(s), 3-indolyl thio-acetate derivatives, arginine-derived nitric oxide biosynthesis inhibitors, dicyclic amine derivatives, spiroisoindole derivatives, imidazo(1,2-A)-pyridinylalkyl, 1,2,3,4-tetrahydro-9H-pyridoindole or benzothiophene derivatives, indole-2,3-dione-3-oxime derivatives, 1-aryl-2-(aminomethyl)cyclopropanecarboxamide derivatives, 4-phosphono-2-amino-alkenoic acid derivatives, naphthopyran derivatives, beta-ketone, beta oxime or beta hydrazine phosphonate, topa quinone amino acid, kynurenic acid, quinoline- or thienopyridine-carboxylic acid derivatives, 10,5-(imino-methano)-10,11-dihydro-5H-dibenzo(A,D)cycloheptene or its derivatives, bicyclic amino-hydroxamate derivatives, indole-2-carboxylic acid derivatives, substituted adamantane derivatives, benzobicycloalkane derivatives, 2,4-disubstituted-1,2,3,4-tetrahydro-quinoline derivatives, dihydro-alkyl-substituted-(immunomethano)-5H-dibenzo-cycloheptene, aryl-cyclohexylamine, N-substituted. benzobicycloalkane amine, isoquinoline phosphonates, N,N'-disubstituted.-guanidine, phosphonopropenyl piperidine carboxylic acid, (2R,3S,4S)-alpha-carboxy-cyclopropyl-glycine, pyrrolidine derivatives, dihydroxy-fused heterocyclyl quinoxaline derivatives, hydrogenated derivatives of MK 801 and analogues, 5-substituted 10,11-dihydro 5H-dibenzo(a,d)cycloheptene5,10-imine, 11-exo-hydroxy MK 801 preparations, tetra hydroisoquinoline or 2-benzazepine derivatives, N-3-phenyl-propionyl-substituted. spermine or related polyamine derivatives, 4-amino-fluorene or its heterocyclic analogues, cyclooctane-imine derivatives, R-3-amino-1-hydroxy pyrrolidin-2-one or methionine hydroxamate, 10,11-dihydro-5H-dibenzo-cyclohepten-5,10-imine, polyhydro-10,11-dihydro-5H-benzo(a,d)cyclohepten-5,10 imine derivatives, 4-oxo-1,4-dihydroquinoline with 2-acidic groups, heterocyclyl-alkene-phosphonic acid, phosphono group-containing pyridine 2-carboxylic acid, alpha-amino-alpha-(3-alkylphenyl)alkyl ethanoic acid, its esters or amides, 10,11-dihydro-5H-dibenzo-A,D-cyclohepten-5,10-imine, phosphorus containing unsaturated amino acids or their salts, 5 substituted-1-,11-dihydro-5H-dibenzo-cyclohepten-5,10-imine or analogues, heterocyclic phosphonic acid derivatives or their salts, substituted 4-(amino-carbonyl-amino)quinoline derivatives, tricyclic quinoxaline derivatives, butyryl-tyrosine spermine or one of its analogues, tri- or tetra-substituted guanidine, quinoxalinylalkyl-aminoalkane phosphonic acid derivatives, 2-(aminophenyl)-3-(2-carboxy-indol-3-yl)-propenoic acid derivatives, 6-piperidinylpropionyl-2(3H)-benzoxazolone derivatives, 6-(3-[4-(4-fluorobenzyl)piperidin-1-yl]propionyl)-3H-benzoxazol-2-one or its salts, imidazo(1,2-a)pyridine, tetrahydroquinoline derivatives or their salts, 2-methyl-5,8-substituted 2,3,4,5-tetra- or 2,3,4,4a,5,9b-hexahydro-1H-pyrido[4,3-b]indole, 3-aminoindolyl, 6-pyrrolyl-quinoxaline-2,3-dione derivatives, imidazolyl-(mercaptoalkyl)-quinoxaline-dione, 3-amidoindolyl derivatives, heterocyclyl-imidazolo-quinoxalinone, naphthyl-substituted alpha-amino acid derivatives, 5-hetero-aryl-2,3-quinoxaline-dione derivatives, quinoxaline derivatives, 5H,10H-imidazo indeno 4-pyrazinone derivatives, hydroxy-(aryl-substituted phenyl)-quinolone, imidazo indolo pyrazinone derivatives, ((phenyl-amino)-(m)ethyl)-pyridine derivatives, tetrahydro-isoquinoline derivatives, 4-substituted piperidine analogues, 2-substituted piperidine derivatives, tri- or tetra-substituted guanidine derivatives, 3-hydroxy-4-imidazolidinone, 3-aminoquinoxalin-2-one derivatives, 1-amino-1-cyclobutanecarboxylic acid, thiamorphinan derivatives, pyrido[4,3-b]indole derivatives, 4-phenyl carbamoyl methylene tetrahydro quinoline-2-carboxylic acid or derivatives thereof, (3R,4S)-3-(4-(4-fluorophenyl)-4-hydroxy-piperidin-1-yl)-chroman-4,7-diol, indeno-pyrazin-4-one, 2,3-dioxo-1,2,4,5-tetrahydro-quinoxalinyl derivatives, 4,5-bridged quinoxalinedione or quinolone, (1S,2S)-1-(4-hydroxyphenyl)2-(4-hydroxy 4-phenyl piperidin-1-yl) 1-propanol methane sulphonate trihydrate, 4-sulphanimide-quinoline derivatives, methanobenzocyclodecen-13-amine, quinoxalinyl-(alkane, alkene, or alkyne)-phosphonic acid derivatives and esters, diarylalkylamine related to spider and wasp venom toxins, piperazine R-alpha-carboxylic acid derivatives, imidazo-indeno-pyrazin-4-one derivatives, pyridazino-quinoline derivatives, 1-substituted or 1,3-di-substituted 1,3-diaryl-guanidine, aza-cycloalkyl-fused quinoxaline-dione, 3-substituted 2-carboxy-indole derivatives or intermediates, (2R)—N-trityl-4-oxo-5-(dimethyl phosphono)-nor-valinate ester, kynurenic acid derivatives, indole carboxylic acid derivatives, 6-(tetrazolyl or isoxazolyl)-decahydroisoquinoline-3-carboxylic acid derivatives, phenyl- or pyridinyl-thieno-pyridinone derivatives, fused cycloalkyl-quinoxaline-dione derivatives, pyridazino-quinoline derivatives, 1-alpha-amino-3-biphenyl-propanoic acid derivatives, 3-(Indol-3-yl)propenoic acid derivatives, spiro-heterocycle-imidazo-indeno-pyrazine-4-one derivatives, 2-heterocyclyl-3-indolylpropenoic acid derivatives, piperidinoalkyl heterocyclic ketone, pyrrolyl-tetrahydro-benzoquinoxaline-dione derivatives, 7-imidazolyl or dialkylamino, tetrahydroquinoxaline dione, dibenzocycloheptene, quinoxaline derivatives, aryl-thio-quinoxaline derivatives, heterocyclic substituted imidazolo-quinoxaline derivatives, 1,4-dihydro-quinoxaline-2,3-dione derivatives, oxa- or thia-aliphatically bridged quinoxaline derivatives, aza-aliphatically bridged quinoxaline-2,3-dione, 3-amido- or 3-sulphamido-indole, 3,5-disubstituted phenyl-naphthalene derivatives, imidazo (1,2-a)indeno (1,2-e) pyrazine-2-carboxylic acid derivatives, 3-phenyl-fused ring pyridine-dione derivatives, 2-phenyl-pyridazino-indole-dione derivatives, 4,6-disubstituted kynurenine, phosphono derivatives of imidazo(1,2-a)pyrimidine-2-carboxamide, tetrahydro-quinoxaline-dione derivatives with N-(alkyl)carbonyl-amino- or ureido group, tryptophan derivatives, hetero-aliphatic or heteroaraliphatic substituted quinolone derivatives, imidazopyridine dicarboxylic acid derivatives, compositions containing pyrazolo-quinoline derivatives, ethanodihydrobenzoquinolizinium salt, oxopyridinylquinoxaline derivatives, indeno-triazolo-pyrazin-4-one derivatives, imidazo-indeno-pyrazinone derivatives, imidazo-indeno-pyrazin-4-one derivatives, imidazo(1,2-a)pyrazine-4-one derivatives, 5H-indeno-pyrazine-2,3-dione derivatives, phenyl-aminoalkyl-cyclopropane N,N-diethyl carboxamide, dexanabinol derivatives, substituted chroman derivatives, sulphonamide quinazoline-2-4-dione, 6- and 8-aza-, and 6,8-diaza-1,4-dihydro-quinoxaline-2,3-dione derivatives, substituted quinoline derivatives, tetrazolylalkyl cyclohexyl aminoalkanoic acid, tricyclic indole 2-carboxylic acid derivatives, 6-substituted-7H-imidazo-8-pyrazinone derivatives, tricyclic pyridazinopyridine derivatives, N-substituted heterocyclylidenemethyl-indole carboxylic acid derivatives, 3-aza-8-substituted-bicyclo(3.3.0)octane-2-carboxylic acid derivatives, ethano-heterocyclo-isoquinolinium, phenyl alkanolamine derivatives, dihydrobenzothiadiazinedioxide carboxylic acid derivatives, methyl-butenylmethyl(hydroxypropyl)carbazoledione, imidazo pyrazinone derivatives, imidazo-(1,2-a)pyrazine-4-one, benzazepine-dione derivatives, disulfiram, 3-(indol-3-yl)-propenoic acid derivatives, 1,2,3,4-tetrahydro-quinoline-2,3,4-trione-3 or 4-oxime, 2-amino-2-phenyl(alkyl)-acetic acid derivatives, 6-halo-tryptophan or a 4-halo-kynurenine, 6-tetrazolyl or isoxazolyl-decahydro-isoquinoline-3-carboxylic acid derivatives, or imidazolyl-benzene or salts thereof.

NMDA-R Channel Blockers

NMDA receptor channel blockers refer to compounds that reduce the permeability of channels associated with the NMDA receptor to cations (e.g., to $Na^+$, $K^+$ and/or $Ca^{2+}$ ions). NMDA receptor channel blockers can therefore be used to prevent a signal being transmitted due to ionic flux that would otherwise occur when glutamate binds to the NMDA receptor.

NMDA receptor channel blockers include e.g., magnesium, dizocilpine, phencyclidine, ketamine, memantine, tiletamine, budipine, flupirtine, 1-[1-(2-thienyl)cyclohexyl]piperidine (TCP), and (+)-(3S,4S)-7-hydroxy-delta6-tetrahydrocannabinol-1,1-dimethylheptyl (HU211).

AMPA-R Agonists

AMPA-R agonists include, e.g., benzoxazapines such as those described in U.S. Pat. No. 7,307,073; N-anisoyl-2-pyrrolidinone; sulphonamides such as cyclothiazide; aniracetam derivatives such as those disclosed in WO 94/02475; benzoylpiperidines and pyrrolidines such as those disclosed in WO 96/38414; AMPA-R agonist compounds disclosed in WO 97/36907; AMPA-R agonist compounds disclosed in WO 99/51240; 1,2,4-benzothiadiazine-1,2-dioxides, that are structural derivatives of cyclothiazide™, as disclosed in WO 99/42456; and the like.

AMPA-R Antagonists

AMPA-R antagonists refer to compounds that bind to AMPA receptors in a competitive manner or interact with AMPA receptor associated sites and block AMPA mediated signal in a non-competitive manner AMPA antagonists include L-glutamate derivatives, amino alkanoic acid derivatives, α-amino-3-hydroxy-5-methyl-4-isoxazolepropionate derivatives, acetyl-aminophenyl-dihydro-methyl-dioxolobenzodiazepine, acid amide derivatives, amino-phenyl-acetic acid, 2,3-benzodiazepin-4-one, alkoxy-phenyl-benzodiazepine, amino- or desamino-2,3-benzodiazepine, benzothiadiazine, .beta.-carboline-3-carboxylic acid, fused cycloalkylquinoxalinediones, decahydroisoquinoline, 4-hydroxypyrrolone, 4-hydroxy-pyrrolo-pyridazinone, imidazo-pyrazinone, imidazolo-quinoxalinone, indeno-pyrazine-carboxylic acid, indeno-pyrazinone, indoloneoxime, indolo-pyrazinone, isatine, isatinoxime, oxadiazole, phenylazolophthalazine, phenylpyridazino-indole-1,4-dione, quinoline, quinolinone, quinoxaline, quinoxalinedione, quinazolinone, quinolone, nitroquinolone, and sulphamate derivatives.

AMPA-R Channel Blockers

AMPA receptor channel blockers refer to compounds that reduce the permeability of channels associated with the AMPA receptor to cations (e.g., to $Na^+$, $K^+$ and/or $Ca^{2+}$ ions). AMPA receptor channel blockers can therefore be used to prevent a signal being transmitted due to ionic flux that would otherwise occur when glutamate binds to the AMPA receptor.

AMPA receptor channel blockers include e.g. fluorowillardiine, Joro spider toxin, NSTX spider toxin, and argiotoxin.

KA-R Agonists

KA-R agonists include glutamate, domoic acid, kainic acid, LY339434, methyl glutamate, 4-allyl glutamate, etc.

KA-R Antagonists

KA receptor antagonists refer to compounds that bind to KA receptors in a competitive manner or interact with KA receptor associated sites and block KA mediated signal in a non-competitive manner.

KA-R antagonists include L-glutamate derivatives, kainic acid derivatives, acid amide derivatives, aminoalkanoic acid derivatives, aminophenyl(alkyl)acetic acid derivatives, fused cycloalkylquinoxalinediones, quinoxalinedione, imidazolo-quinoxalinone, isatine, phenyl-azolophthalazine, pyridothiazines, 4-phosphonoalkyl-quinolinone, quinolinone, quinazoline, quinazolinedione, quinoxalinedione and sulphamate derivatives.

KA-R Channel Blockers

KA-R channel blockers refer to compounds that reduce the permeability of channels associated with the KA receptor to cations (e.g., to $Na^+$, $K^+$ and/or $Ca^{2+}$ ions). KA receptor channel blockers can therefore be used to prevent a signal being transmitted due to ionic flux that would otherwise occur when glutamate binds to the KA receptor. KA-R channel blockers include, e.g., Joro spider toxin, NSTX spider toxin, and argiotoxin 636.

mGluR Agonists mGluR agonists, include, e.g., (2S,1'S,2'S)-2-(2-carboxycyclopropyl)glycine, also known as L-CCG-I; (2S,1'S,2'R,3'R)-2-(2'-carboxy-3'-(methoxymethyl)cyclopropyl-glycine, also known as cis-MCG-I; (2S,1'S,2'R,3'S)-2-(2'-carboxy-3'-(methoxymethyl)cyclopropylglycine, also known as trans-MCG-I; (2S,1'R,2'R,3'R)-2-(2',3'-dicarboxy-cyclopropyl) glycine, also known as DCG-IV; 2-carboxy-3,3-dihalocyclopropylglycines, including (2S,1'S,2'S)-2-(2-carboxy-3,3-difluoro)-cyclopropylglycine (see, e.g., WO 98/00391); 1-aminocyclopentane-1,3-dicarboxylic acid; 2-amino-2-(3,5-dihydroxyphenyl)-acetic acid; quisqualate; ibotenate. (S)-4-carboxy-3-hydroxyphenylglycine; (S)-4-Carboxyphenylglycine; LY341495 ((1R,2R)-2-[(1R)-1-amino-1-carboxy-2-(2,6-dioxo-3H-purin-9-yl)ethyl]cyclopropane-1-carboxylic acid); LY367385 (2-methyl-4-carboxy-5-hydroxyphenylglycine); etc.

mGluR Antagonists mGluR antagonists include, e.g., 2S,1'S,2'S,3'R)-2-(2'-carboxy-3'-phenylcyclopropyl)glycine, also known as PCCG 4; etc.

Compositions

The present invention further provides compositions comprising a subject synthetic regulator. Compositions comprising a subject synthetic regulator will in many embodiments include one or more of: a salt, e.g., NaCl, MgCl, KCl, $MgSO_4$, etc.; a buffering agent, e.g., a Tris buffer, N-(2-Hydroxyethyl) piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, Nonidet-P40, etc.; a protease inhibitor; and the like. In some embodiments, a subject composition comprising a subject synthetic regulator is a pharmaceutical composition, as described in more detail below.

Light-Regulated Glutamate Receptors

The present invention further provides a light-regulated glutamate receptor, where a subject light-regulated glutamate receptor comprises a glutamate receptor and a subject synthetic regulator of glutamate receptor function in non-covalent association with the glutamate receptor. The synthetic regulator of glutamate receptor function is non-covalently associated with the glutamate receptor at or near a ligand binding site of the glutamate receptor. In some embodiments, a subject light-regulated glutamate receptor is isolated, e.g., free of other polypeptides or other macromolecules. In other embodiments, a subject light-regulated glutamate receptor is membrane-associated and is present in vitro. In other embodiments, a subject light-regulated glutamate receptor is present in a living cell in vitro or in vivo. In other embodiments, a subject light-regulated glutamate receptor is present in a membrane of a living cell in vitro or in vivo. In other embodiments, a subject light-regulated glutamate receptor is present in a living cell in a tissue in vitro or in vivo. In other embodiments, a subject light-regulated glutamate receptor is present in a living cell in a multicellular organism.

A change in the wavelength and/or intensity of light ($\Delta\lambda$) to which the light-regulated glutamate receptor is exposed results in a change in ligand binding to a ligand-binding site of the light-regulated glutamate receptor, e.g., results in a change in binding of the ligand portion of the synthetic regulator to the ligand-binding site of the light-regulated glutamate receptor. A "change in the wavelength of light to which the light-regulated glutamate receptor is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. Repetitive changing from $\lambda_1$ to $\lambda_2$, then from $\lambda_2$ to $\lambda_1$, and back, e.g., switching from a first wavelength to a second wavelength, and back again repeatedly, is also contemplated. Repetitive changing from light to darkness, from darkness to light, etc., is also contemplated.

In some embodiments, the change in wavelength (from $\lambda_1$ to $\lambda_2$; from light to darkness; or from darkness to light) results in a change in binding of the ligand to a ligand-binding site. As used herein, a "change in binding of a ligand to a ligand-binding site" includes increased binding and decreased binding. As used herein, "increased binding" includes one or more of: an increased probability of binding of the ligand to the ligand-binding site; an increased binding affinity of the ligand for the ligand-binding site; an increased local concentration of the ligand at the ligand-binding site; and an increased occupancy of the ligand in the ligand-binding site. As used herein, "decreased binding" includes one or more of: a decreased probability of binding of the ligand to the ligand-binding site; a decreased binding affinity of the ligand for the ligand-binding site; a decreased local concentration of the ligand at the ligand-binding site; and a decreased occupancy of the ligand in the ligand-binding site. As used herein, the term "change in wavelength" to which a synthetic regulator is exposed, or to which a glutamate receptor/synthetic light regulator complex is exposed, refers to a change in wavelength from $\lambda_1$ to $\lambda_2$; a change from light to darkness; or a change from darkness to light. An increase in binding includes an increase of from about 10% to about 50%, from about 50% to about 2-fold, from about 2-fold to about 5-fold, from about 5-fold to about 10-fold, from about 10-fold to about 50-fold, from about 50-fold to about $10^2$-fold, from about $10^2$-fold to about $10^4$-fold, from about $10^4$-fold to about $10^6$-fold, from about $10^6$-fold to about $10^8$-fold, or a greater than $10^8$-fold increase in binding. A decrease in binding includes a decrease of from about 5% to about 10% to about 20% to about 30%, from about 30% to about 40%, from about 40% to about 50%, from about 50% to about 60%, from about 60% to about 70%, from about 70% to about 80%, from about 80% to about 90%, or from about 90% to 100% decrease in binding.

For example, in some embodiments, the ligand has a first probability of binding to the ligand site at a first wavelength of light; the ligand has a second probability of binding to the ligand binding site at a second wavelength of light; and the second probability is lower than the first probability. In other embodiments, the ligand has a first probability of binding to the ligand site at a first wavelength of light; the ligand has a second probability of binding to the ligand binding site at a second wavelength of light; and the second probability is higher than the first probability. In other embodiments, ligand has a first probability of binding to the ligand site when exposed to light; the ligand has a second probability of binding to the ligand binding site in the absence of light (e.g., in darkness); and the second probability is lower than the first probability. In other embodiments, the ligand has a first probability of binding to the ligand site when exposed to light; the ligand has a second probability of binding to the ligand binding site in the absence of light and the second probability is higher than the first probability.

The local concentration of the ligand portion of the synthetic regulator at the ligand binding site in a subject light-regulated glutamate receptor is high. For example, the local concentration of the ligand portion of the synthetic regulator at the ligand binding site in a subject light-regulated glutamate receptor ranges from about 500 nM to about 50 mM, e.g., from about 500 nM to about 750 nM, from about 750 nM to about 1 mM, from about 1 mM to about 5 mM, from about 5 mM to about 10 mM, from about 10 mM to about 20 mM, from about 20 mM to about 30 mM, or from about 30 mM to about 50 mM.

Change in Wavelength Resulting in Binding of the Ligand to the Ligand-Binding Site or Higher Affinity Ligand Binding to Ligand-Binding Site In some embodiments, a change in the wavelength of light to which the light-regulated glutamate receptor is exposed results in an increase in binding affinity of the ligand portion of a subject synthetic regulator for a ligand-binding site of the light-regulated glutamate receptor. For example, in some embodiments, a change in wavelength of light to which the light-regulated glutamate receptor is exposed results in an at least about 10%, at least about 20%, at least about 30%, at least about 50%, at least about 75%, at least about 2-fold, at least about 5-fold, at least about 10-fold, at least about 25-fold, at least about 50-fold, at least about 100-fold, at least about 250-fold, at least about 500-fold, at least about $10^3$-fold, at least about $5 \times 10^3$-fold, at least about $10^4$-fold, at least about $5 \times 10^4$-fold, or greater, increase in binding affinity.

Where the ligand is an agonist, the change in wavelength will in some embodiments result in activation of the light-regulated glutamate receptor. Where the ligand is an agonist, the change in wavelength will in some embodiments result in desensitization of the light-regulated glutamate receptor. Conversely, where the ligand is an antagonist, the change in wavelength results in a block of activation of the light-regulated glutamate receptor, e.g., block of the ability to activate the light-regulated glutamate receptor with free agonist. Where the ligand is a blocker (e.g., a pore blocker of an ion channel, or an interaction domain that binds to other biological macromolecules such as polypeptides or nucleic acids), the change in wavelength results in block of glutamate receptor activity.

Expressed another way, where the ligand is an agonist, and where a change in the wavelength of light to which the light-regulated glutamate receptor is exposed results in a higher binding affinity of the ligand moiety of the synthetic regulator to the ligand-binding site of the light-regulated glutamate receptor, the change in wavelength results in transition from an inactive state to an active state, or to a desensitized state. Where the ligand is an antagonist, the change in wavelength results in transition from a responsive state to an unresponsive state. Where the ligand is a blocker, the change in wavelength results in transition from an active state to an inactive state.

Change in Wavelength Resulting in Removal of Ligand from Ligand-Binding Site, or Reduced Binding Affinity In some embodiments, a change in the wavelength of light to which the light-regulated glutamate receptor is exposed results in removal of the ligand portion of a subject synthetic regulator from a ligand-binding site of the light-regulated glutamate receptor, e.g., the ligand is not bound to the ligand-binding site. In some embodiments, a change in the wavelength of light to which the light-regulated glutamate receptor is exposed results in reduced binding affinity of the ligand portion of a subject synthetic regulator for a ligand-binding site of the light-regulated glutamate receptor, e.g., the ligand has reduced binding affinity for the ligand-binding site. For example, in some embodiments, a change in the wavelength of light to which the light-regulated glutamate receptor is exposed results in a reduction of binding affinity of at least about 10%, at least about 20%, at least about 25%, at least about 30%, at least about 40%, at least about 50%, at least about 60%, at least about 70%, at least about 80%, at least about 90%, at least about 95%, or more.

Where the ligand is an agonist, the change in wavelength will in some embodiments result in deactivation of the light-regulated glutamate receptor. Where the ligand is an agonist, the change in wavelength will in some embodiments result in recovery from desensitization of the light-regulated glutamate receptor. Conversely, where the ligand is an antagonist, the change in wavelength results in activation of the light-regulated glutamate receptor, or results in removal of a blocker from the light-regulated glutamate receptor. Where the ligand is a blocker (e.g., a pore blocker of an ion channel, or an interaction domain that binds to other biological macromolecules such as polypeptides or nucleic acids), the change in wavelength results in relief of a block in glutamate receptor activity and permits the glutamate receptor to function normally.

Expressed another way, where the ligand is an agonist, and where a change in the wavelength of light to which the light-regulated glutamate receptor is exposed results in removal (or non-binding) of the ligand moiety of the synthetic regulator from the ligand-binding site of the light-regulated glutamate receptor, the change in wavelength results in transition from an active state to an inactive state, or from a desensitized state to a responsive state. Where the ligand is an antagonist, the change in wavelength results in transition from an unresponsive state to a responsive state. Where the ligand is a blocker, the change in wavelength results in transition from an inactive state to an active state.

Compositions

The present invention further provides compositions comprising a subject light-regulated glutamate receptor. Compositions comprising a subject light-regulated glutamate receptor will in many embodiments include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

Cells

The present invention further provides a cell comprising a subject light-regulated glutamate receptor. A subject cell finds use in a variety of applications, e.g., screening applications, such as identification of agents that modulate the activity of a glutamate receptor; and research applications such as examination of a physiological event. Where the cell is used in a screening assay, the cell can be referred to as a "test cell."

In some embodiments, the cell is a eukaryotic cell in vitro cell culture, and is grown as an adherent monolayer, or in suspension. In other embodiments, the cell is a eukaryotic cell and is part of a tissue or organ, either in vivo or in vitro. In other embodiments, the cell is a eukaryotic cell and is part of a living multicellular organism, e.g., a protozoan, an amphibian, a reptile, a plant, an avian organism, a mammal, a fungus, an algae, a yeast, a marine microorganism, a marine invertebrate, an arthropod, an isopod, an insect, an arachnid, etc. In other embodiments, the cell is a prokaryotic cell.

In other embodiments, the cell is a member of archaea, e.g., an archaebacterium. Archaebacteria include a methanogen, an extreme halophile, an extreme thermophile, and the like. Suitable archaebacteria include, but are not limited to, any member of the groups Crenarchaeota (e.g., *Sulfolobus solfataricus, Defulfurococcus mobilis, Pyrodictium occultum, Thermofilum pendens, Thermoproteus tenax*), Euryarchaeota (e.g., *Thermococcus celer, Methanococcus thermolithotrophicus, Methanococcus jannaschii, Methanobacterium thermoautotrophicum, Methanobacterium formicicum, Methanothermus fervidus, Archaeoglobus fulgidus, Thermoplasma acidophilum, Haloferax volcanni, Methanosarcina barkeri, Methanosaeta concilli, Methanospririllum hungatei, Methanomicrobium mobile*), and Korarchaeota.

In some embodiments, the cell is of a particular tissue or cell type. For example, where the organism is a plant, the cell is part of the xylem, the phloem, the cambium layer, leaves, roots, etc. Where the organism is an animal, the cell will in some embodiments be from a particular tissue (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

A subject cell is in many embodiments a unicellular organism, or is grown in culture as a single cell suspension, or as monolayer. In some embodiments, a subject cell is a eukaryotic cell. Suitable eukaryotic cells include, but are not limited to, yeast cells, insect cells, plant cells, fungal cells, mammalian cells, and algal cells. Suitable eukaryotic host cells include, but are not limited to, *Pichia pastoris, Pichia fin-*

*landica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. In some embodiments, the neuronal cell is a primary cell isolated from an animal. In some embodiments, the neuronal cell or neuronal-liked cell is an immortalized cell line. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In other embodiments, the host cell is a plant cell. Plant cells include cells of monocotyledons ("monocots") and dicotyledons ("dicots"). Guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

Suitable prokaryotic cells include bacteria (e.g., Eubacteria) and archaebacteria. Suitable archaebacteria include a methanogen, an extreme halophile, an extreme thermophile, and the like. Suitable archaebacteria include, but are not limited to, any member of the groups Crenarchaeota (e.g., *Sulfolobus solfataricus, Defulfurococcus mobilis, Pyrodictium occultum, Thermofilum pendens, Thermoproteus tenax*), Euryarchaeota (e.g., *Thermococcus celer, Methanococcus thermolithotrophicus, Methanococcus jannaschii, Methanobacterium thermoautotrophicum, Methanobacterium formicicum, Methanothermus fervidus, Archaeoglobus fulgidus, Thermoplasma acidophilum, Haloferax volcanni, Methanosarcina barkeri, Methanosaeta concilli, Methanospririllum hungatei, Methanomicrobium mobile*), and Korarchaeota. Suitable eubacteria include, but are not limited to, any member of Hydrogenobacteria, Thermotogales, Green non-sulfphur bacteria, Denococcus Group, Cyanobacteria, Purple bacteria, Planctomyces, Spirochetes, Green Sulphur bacteria, Cytophagas, and Gram positive bacteria (e.g., *Mycobacterium* sp., *Micrococcus* sp., *Streptomyces* sp., *Lactobacillus* sp., *Helicobacterium* sp., *Clostridium* sp., *Mycoplasma* sp., *Bacillus* sp., etc.).

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the cell is *Escherichia coli*.

Membranes

The present invention further provides a membrane comprising a subject light-regulated glutamate receptor. In some embodiments, the membrane is a biological membrane (e.g., a lipid bilayer surrounding a biological compartment such as a cell, including artificial cells, or a membrane vesicle or sheet). In some embodiments, the membrane is part of a living cell, as described above. In other embodiments, the membrane is an artificial (synthetic) membrane, e.g., a planar membrane, a liposome, etc.

In some embodiments, the artificial membrane is a lipid bilayer. In other embodiments, the artificial membrane is a lipid monolayer. In some embodiments, the artificial membrane is part of a liposome. Liposomes include unilamellar vesicles composed of a single membrane or lipid bilayer, and multilamellar vesicles (MLVs) composed of many concentric membranes (or lipid bilayers).

Artificial membranes, and methods of making same, have been described in the art. See, e.g., U.S. Pat. No. 6,861,260; Kansy et al. (1998) *J. Med. Chem.* 41 (7):1007-10; and Yang et al. (1996) *Advanced Drug Delivery Reviews* 23:229-256.

A subject artificial membrane will in some embodiments, include one or more phospholipids. In some embodiments, the artificial membrane comprises a mixture of phospholipids containing saturated or unsaturated mono or disubstituted fatty acids and a combination thereof. These phospholipids are in some embodiments selected from dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, and palmiticlinoleoylphosphatidic acid. Suitable phospholipids also include the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in such lysophosphatidyl derivatives will in some embodiments be palimtoyl, oleoyl, palmitoleoyl, linoleoyl myristoyl or myristoleoyl.

Methods of Modulating Protein Activity

The present invention provides methods of modulating glutamate receptor activity. In certain aspects, the present invention provides methods of modulating activity of a subject light-regulated glutamate receptor, where the method generally involves changing the wavelength of light to which the light-regulated glutamate receptor is exposed. In certain aspects, the present invention provides methods of modulating activity of a glutamate receptor, where the method generally involves: a) contacting the glutamate receptor with a subject synthetic regulator, where the synthetic regulator binds to the glutamate receptor, thereby generating a light-regulated glutamate receptor; and b) changing the wavelength of light to which the light-regulated glutamate receptor is exposed.

As noted above, a "change in the wavelength of light to which the light-regulated glutamate receptor is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. In certain aspects, the present invention provides methods of modulating activity of a native (wild-type) glutamate receptor, where the method generally involves: a) contacting a glutamate receptor with a subject synthetic regulator, where the subject synthetic regulator binds to the glutamate receptor, forming a synthetic regulator/glutamate receptor complex; and b) changing the wavelength of light to which the synthetic regulator/glutamate receptor complex is exposed. As noted above, a "change in the wavelength of light to which the light-regulated glutamate receptor is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. The synthetic regulator/glutamate receptor complex is also referred to as a "light-regulated glutamate receptor."

In some embodiments, the glutamate receptor or the light-regulated glutamate receptor is present in a cell-free in vitro system, e.g, the glutamate receptor or the light-regulated glutamate receptor is not associated with a cell. In other embodiments, the glutamate receptor or the light-regulated glutamate receptor is associated with a cell, e.g., the glutamate receptor or the light-regulated glutamate receptor is integrated into a cell membrane in a cell, the glutamate receptor or the light-regulated glutamate receptor is in the cytosol of a cell, the glutamate receptor or the light-regulated glutamate receptor is in an intracellular organelle, etc. In other embodiments, the glutamate receptor or the light-regulated glutamate receptor is in a synthetic membrane, e.g., in a planar synthetic membrane, in a liposome, in a membrane of an artificial cell, etc. In some embodiments, the cell-associated glutamate receptor or the cell-associated light-regulated glutamate receptor is in a cell in vitro, e.g., in a cell in a monolayer, in a cell in suspension, in an in vitro tissue, etc. In other embodiments, the cell-associated glutamate receptor or the cell-associated light-regulated glutamate receptor is in a cell in vivo, e.g., in a cell of an organism, e.g., a living organism.

In some embodiments, the change in wavelength (from $\lambda_1$ to $\lambda_2$; from light to darkness; or from darkness to light) results in a change in binding of the ligand to a ligand-binding site. As used herein, a "change in binding of a ligand to a ligand-binding site" includes increased binding and decreased binding. As used herein, "increased binding" includes one or more of: an increased probability of binding of the ligand to the ligand-binding site; an increased binding affinity of the ligand for the ligand-binding site; an increased local concentration of the ligand at the ligand-binding site; and an increased occupancy of the ligand in the ligand-binding site. As used herein, "decreased binding" includes one or more of: a decreased probability of binding of the ligand to the ligand-binding site; a decreased binding affinity of the ligand for the ligand-binding site; a decreased local concentration of the ligand at the ligand-binding site; and a decreased occupancy of the ligand in the ligand-binding site. As used herein, the term "change in wavelength" to which a synthetic regulator is exposed, or to which a glutamate receptor/synthetic light regulator complex is exposed, refers to a change in wavelength from $\lambda_1$ to $\lambda_2$; a change from light to darkness; or a change from darkness to light. An increase in binding includes an increase of from about 10% to about 50%, from about 50% to about 2-fold, from about 2-fold to about 5-fold, from about 5-fold to about 10-fold, from about 10-fold to about 50-fold, from about 50-fold to about $10^2$-fold, from about $10^2$-fold to about $10^4$-fold, from about $10^4$-fold to about $10^6$-fold, from about $10^6$-fold to about $10^8$-fold, or a greater than $10^8$-fold increase in binding. A decrease in binding includes a decrease of from about 5% to about 10% to about 20% to about 30%, from about 30% to about 40%, from about 40% to about 50%, from about 50% to about 60%, from about 60% to about 70%, from about 70% to about 80%, from about 80% to about 90%, or from about 90% to 100% decrease in binding.

For example, in some embodiments, the ligand has a first probability of binding to the ligand site at a first wavelength of light; the ligand has a second probability of binding to the ligand binding site at a second wavelength of light; and the second probability is lower than the first probability. In other embodiments, the ligand has a first probability of binding to the ligand site at a first wavelength of light; the ligand has a second probability of binding to the ligand binding site at a second wavelength of light; and the second probability is higher than the first probability. In other embodiments, ligand has a first probability of binding to the ligand site when exposed to light; the ligand has a second probability of binding to the ligand binding site in the absence of light (e.g., in darkness); and the second probability is lower than the first probability. In other embodiments, the ligand has a first probability of binding to the ligand site when exposed to light; the ligand has a second probability of binding to the ligand binding site in the absence of light and the second probability is higher than the first probability.

A change in wavelength can result in a change in activity of the light-regulated protein. "Activity" will depend, in part, on the glutamate receptor, and can include activity of an ion channel; activity of a receptor in transmitting a signal; etc.

In some embodiments, the change in wavelength results in binding of the ligand to the ligand-binding site of the glutamate receptor. In some embodiments, the change in wavelength results in increased binding affinity of the ligand to the ligand-binding site for the glutamate receptor. In these embodiments, where the ligand is an agonist, and the change results in activation of said glutamate receptor; and where the ligand is an antagonist, the change results in block of activation of the glutamate receptor; and where the ligand is an active site or pore blocker, the change results in inhibition of the glutamate receptor; and where the ligand is a blocker of a site of interaction with other macromolecules, the change interferes with that interaction. In some embodiments, prolonged binding of an agonist to the ligand-binding site results in desensitization or inactivation of the glutamate receptor. In other embodiments, binding of an antagonist blocks activation of the glutamate receptor.

In other embodiments, the change in wavelength results in lack of binding of the ligand to the ligand-binding site, e.g., removal of the ligand from the ligand-binding site of the glutamate receptor. In other embodiments, the change in wavelength results in reduced binding affinity of the ligand for the ligand-binding site, e.g., reduced binding affinity of ligand for the ligand-binding site of the glutamate receptor. In these embodiments, where the ligand is an antagonist, the change results in activation of said glutamate receptor; and where the ligand is an agonist, the change results in deactivation of light-regulated glutamate receptor, or recovery from desensitization or inactivation.

In some embodiments, the glutamate receptor is exposed to light of a first wavelength, where exposure to light of the first wavelength ($\lambda_1$) results in binding of the ligand to the ligand-binding site (or increased binding affinity of the ligand for the ligand-binding site); and the glutamate receptor is subsequently exposed to light of a second wavelength ($\lambda_2$), where exposure to light of the second wavelength results in removal of the ligand from the ligand-binding site (or reduced binding affinity of the ligand for the ligand-binding site). This change in wavelength from a first wavelength to a second wavelength ($\Delta\lambda$) can be repeated numerous times, such that the light is switched back and forth between $\lambda_1$ and $\lambda_2$. Switching between $\lambda_1$ and $\lambda_2$ results in switching or transition from a ligand-bound state to a ligand-unbound state.

In some embodiments, the glutamate receptor is exposed to light of a first wavelength, where exposure to light of the first wavelength ($\lambda_1$) results in binding of the ligand to the ligand-binding site (or increased binding affinity of the ligand for the ligand-binding site); and the light is subsequently turned off, e.g., the glutamate receptor is in darkness, where keeping the glutamate receptor in darkness results in removal of the ligand from the ligand-binding site (or reduced binding affinity of the ligand for the ligand-binding site). This change from $\lambda_1$ to darkness can be reversed, e.g., from darkness to $\lambda_1$; and repeated any number of times, as described above. In other embodiments, the glutamate receptor is exposed to light of a first wavelength, where exposure to light of the first wavelength ($\lambda_1$) results in lack of binding of the ligand to the ligand-binding site (or reduced binding affinity of the ligand for the ligand-binding site); and the light is subsequently turned off, e.g., the glutamate receptor is in darkness, where keeping the glutamate receptor in darkness results in binding of the ligand to the ligand-binding site (or increased binding affinity of the ligand for the ligand-binding site). This change from $\lambda_1$ to darkness can be reversed, e.g., from darkness to $\lambda_1$; and repeated any number of times, as described above.

As noted above, the change in wavelength can be repeated any number of times, e.g, from $\lambda_1$ to $\lambda_2$ and from $\lambda_2$ to $\lambda_1$; or from $\lambda_1$ to darkness and from darkness to $\lambda_1$. Thus, a subject method provides for inducing a transition or switch from a ligand-bound state of a protein to a ligand-unbound state of the glutamate receptor, or from a high affinity state to a low affinity state. Depending on whether the ligand is an agonist or an antagonist, the glutamate receptor will in some embodiments be switched from an active state to an inactive (or deactivated) state, or from an inactive (or deactivated) state to an active state.

The wavelength of light to which the light-regulated glutamate receptor is exposed ranges from $10^{-8}$ m to about 1 m, e.g., from about $10^{-8}$ m to about $10^{-7}$ m, from about $10^{-7}$ m to about $10^{-6}$ m, from about $10^{-6}$ m to about $10^{-4}$ m, from about $10^{-4}$ m to about $10^{-2}$ m, or from about $10^{-2}$ m to about 1 m. "Light," as used herein, refers to electromagnetic radiation, including, but not limited to, ultraviolet light, visible light, infrared, and microwave.

The wavelength of light to which the light-regulated glutamate receptor is exposed ranges in some embodiments from about 200 nm to about 800 nm, e.g., from about 200 nm to about 250 nm, from about 250 nm to about 300 nm, from about 300 nm to about 350 nm, from about 350 nm to about 400 nm, from about 400 nm to about 450 nm, from about 450 nm to about 500 nm, from about 500 nm to about 550 nm, from about 550 nm to about 600 nm, from about 600 nm to about 650 nm, from about 650 nm to about 700 nm, from about 700 nm to about 750 nm, or from about 750 nm to about 800 nm, or greater than 800 nm.

In other embodiments, the wavelength of light to which the light-regulated glutamate receptor is exposed ranges from about 800 nm to about 2500 nm, e.g., from about 800 nm to about 900 nm, from about 900 nm to about 1000 nm, from about 1000 nm to about 1200 nm, from about 1200 nm to about 1400 nm, from about 1400 nm to about 1600 nm, from about 1600 nm to about 1800 nm, from about 1800 nm to about 2000 nm, from about 2000 nm to about 2250 nm, or from about 2250 nm to about 2500 nm. In other embodiments, the wavelength of light to which the light-regulated glutamate receptor is exposed ranges from about 2 nm to about 200 nm, e.g., from about 2 nm to about 5 nm, from about 5 nm to about 10 nm, from about 10 nm to about 25 nm, from about 25 nm to about 50 nm, from about 50 nm to about 75 nm, from about 100 nm, from about 100 nm to about 150 nm, or from about 150 nm to about 200 nm.

The difference between the first wavelength and the second wavelength can range from about 10 nm to about 800 nm or more, e.g., from about 10 nm to about 25 nm, from about 25 nm to about 50 nm, from about 50 nm to about 100 nm, from about 100 nm to about 200 nm, from about 200 nm to about 250 nm, from about 250 nm to about 500 nm, or from about 500 nm to about 800 nm. Of course, where the light-regulated glutamate receptor is switched from darkness to light, the difference in wavelength is from essentially zero to a second wavelength.

The intensity of the light can vary from about 1 W/m² to about 50 W/m², e.g., from about 1 W/m² to about 5 W/m², from about 5 W/m² to about 10 W/m², from about 10 W/m², from about 10 W/m² to about 15 W/m², from about 15 W/m² to about 20 W/m², from about 20 W/m² to about 30 W/m², from about 30 W/m² to about 40 W/m², or from about 40 W/m² to about 50 W/m². The intensity of the light can vary from about 1 µW/cm² to about 100 µW/cm², e.g., from about 1 µW/cm² to about 5 µW/cm², from about 5 µW/cm² to about 10 µW/cm², from about 10 µW/cm² to about 20 µW/cm², from about 20 µW/cm² to about 25 µW/cm², from about 25

μW/cm² to about 50 μW/cm², from about 50 μW/cm² to about 75 μW/cm², or from about 75 μW/cm² to about 100 μW/cm². In some embodiments, the intensity of light varies from about 1 μW/mm² to about 1 μW/mm², e.g., from about 1 μW/mm² to about 50 μW/mm², from about 50 μW/mm² to about 100 μW/mm², from about 100 μW/mm² to about 500 μW/mm², from about 500 μW/mm² to about 1 mW/mm², from about 1 mW/mm² to about 250 mW/mm², from about 250 mW/mm² to about 500 mW/mm², or from about 500 mW/mm² to about 1 μW/mm².

In some embodiments, the light-regulated glutamate receptor is regulated using sound, instead of electromagnetic (EM) radiation (light). For example, in some embodiments, the light-regulated glutamate receptor is regulated using ultrasound to effect a change from a first isomeric form to a second isomeric form.

The duration of exposure of the light-regulated glutamate receptor to light can vary from about 1 μsecond (μs) to about 60 seconds (s) or more, e.g., from about 1 μs to about 5 μs, from about 5 μs to about 10 μs, from about 10 μs to about 25 μs, from about 25 μs to about 50 μs, from about 50 μs to about 100 μs, from about 100 μs to about 250 μs, from about 250 μs to about 500 μs, from about 500 μs to about 1 millisecond (ms), from about 1 ms to about 10 ms, from about 10 ms to about 50 ms, from about 50 ms to about 100 ms, from about 100 ms to about 500 ms, from about 500 ms to about 1 second, from about 1 second to about 5 seconds, from about 5 seconds to about 10 seconds, from about 10 seconds to about 15 seconds, from about 15 seconds to about 30 seconds, from about 30 seconds to about 45 seconds, or from about 45 seconds to about 60 seconds, or more than 60 seconds. In some embodiments, the duration of exposure of the light-regulated glutamate receptor to light varies from about 60 seconds to about 10 hours, e.g., from about 60 seconds to about 15 minutes, from about 15 minutes to about 30 minutes, from about 30 minutes to about 60 minutes, from about 60 minutes to about 1 hour, from about 1 hour to about 4 hours, from about 4 hours to about 6 hours, from about 6 hours to about 8 hours, or from about 8 hours to about 10 hours, or longer.

The duration of binding of the ligand portion of the synthetic regulator to the ligand-binding site can vary from less than one second to days. For example, in some embodiments, the duration of binding of the ligand portion of the synthetic regulator to the ligand-binding site varies from about 0.5 second to about 1 second, from about 1 second to about 5 seconds, from about 5 seconds to about 15 seconds, from about 15 seconds to about 30 seconds, from about 30 seconds to about 60 seconds, from about 1 minute to about 5 minutes, from about 5 minutes to about 15 minutes, from about 15 minutes to about 30 minutes, or from about 30 minutes to about 60 minutes. In other embodiments, the duration of binding of the ligand portion of the synthetic regulator to the ligand-binding site varies from about 60 minutes to about 2 hours, from about 2 hours to about 4 hours, from about 4 hours to about 8 hours, from about 8 hours to about 12 hours, from about 12 hours to about 18 hours, from about 18 hours to about 24 hours, from about 24 hours to about 36 hours, from about 36 hours to about 48 hours, from about 48 hours to about 60 hours, from about 60 hours to about 72 hours, from about 3 days to about 4 days, from about 4 days to about 5 days, or from about 5 days to about 7 days, or longer.

Utility

A subject synthetic regulator, a subject light-regulated glutamate receptor, a subject cell, and a subject method of modulating glutamate receptor function, are useful in a wide variety of research applications, pharmaceutical applications, screening assays, therapeutic applications, and the like.

Research Applications

In some embodiments, a subject synthetic regulator or a subject light-regulated glutamate receptor, is useful in studies of cell function, in studies of physiology of whole organisms, and the like.

In physiological studies, changing light exposure of a tissue, organ, or whole organism (or a part of a whole organism) that includes a light-regulated protein provides a method of regulating a function in the tissue, organ, or whole organism. For example, where the light-regulated glutamate receptor is a ligand-gated ion channel, and the synthetic regulator comprises the ligand for the ligand-gated ion channel, changing the wavelength of light to which the light-regulated glutamate receptor is exposed will result in opening or closing of the ion channel, thereby altering ion concentration in cells in a manner that alters their activity (e.g., hormone or neurotransmitter secretion) or state (e.g., transcriptional or translational or metabolic state) or electrical firing, etc.

Screening Methods

The present invention provides methods of identifying an agent that modulates a function (e.g., an activity) of a glutamate receptor. The methods generally involve contacting a light-regulated glutamate receptor with a test agent; and determining the effect, if any, of the test agent on the activity of the light-regulated glutamate receptor (or on the activity of a polypeptide that is regulated by the light-regulated glutamate receptor). The effect, if any, of the test agent on the activity of the light-regulated glutamate receptor is determined by exposing the light-regulated glutamate receptor to light of a first wavelength. In the absence of the test agent, exposure of the light-regulated glutamate receptor to light of a first wavelength induces a transition from a ligand-unbound state to a ligand-bound state. In the presence of a test agent that affects binding of the ligand to the ligand-binding site, the transition from the ligand-unbound state to a ligand-bound state is inhibited.

In some embodiments, the light-regulated glutamate receptor is in vitro in solution (e.g., free of cells or membranes); and the assay is carried out in vitro. In other embodiments, the light-regulated glutamate receptor is in a membrane (e.g., a synthetic membrane) in the absence of a living cell (e.g., in a cell-free system); and the assay is carried out in vitro. In other embodiments, the light-regulated glutamate receptor is in a cell, e.g., a living cell in vitro or in vivo; and in some embodiments, the assay is carried out in vitro, and in other embodiments, the assay is carried out in vivo.

In some embodiments, the light-regulated glutamate receptor is in a cell (e.g., is integrated into the plasma membrane, is in the cytosol of the cell, is in a subcellular organelle, is in the nucleus of the cell, or is integrated into a membrane of a subcellular organelle). In these embodiments, the cell comprising the light-regulated glutamate receptor is a "test cell." The methods generally involve contacting the test cell with a test agent; and determining the effect, if any, of the test agent on the activity of the light-regulated glutamate receptor.

In some embodiments, the test agent is one that inhibits induction of a transition from a first, ligand-bound state to a second, ligand-unbound state. For example, in some embodiments, a test agent of interest is one that inhibits induction of a transition from a first, ligand-unbound state to a second, ligand-bound state by at least about 5%, at least about 10%, at least about 15%, at least about 20%, at least about 25%, at least about 30%, at least about 40%, at least about 50%, at least about 60%, at least about 70%, or at least about 80%, or more, compared to the induction in the absence of the test agent.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising a subject polypeptide (a subject light-regulated glutamate receptor, e.g., a glutamate receptor in a complex with a subject synthetic regulator) in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

The screening methods may be designed a number of different ways, where a variety of assay configurations and protocols may be employed, as are known in the art. The above components of the method may be combined at substantially the same time or at different times. In some embodiments, a subject method will include one or more washing steps.

In some embodiments, the light regulated glutamate receptor is assayed in a membrane-free, cell free assay. In other embodiments, the light regulated glutamate receptor is integrated into an artificial membrane. In other embodiments, light regulated glutamate receptor is integrated into a biological membrane. In other embodiments, the light regulated glutamate receptor is in a living cell, e.g., in the cytosol, in the nucleus, in an intracellular organelle, in the plasma membrane, or in an intracellular membrane of the cell.

Biological cells which are suitable for use in a subject screening assay include, but are not limited to, primary cultures of mammalian cells, transgenic (non-human) organisms and mammalian tissue. Cells in screening assays may be dissociated either immediately or after primary culture. Cell types include, but are not limited to white blood cells (e.g. leukocytes), hepatocytes, pancreatic beta-cells, neurons, smooth muscle cells, intestinal epithelial cells, cardiac myocytes, glial cells, and the like.

Biological cells which are suitable for use in a subject screening assay include cultured cell lines (e.g., immortalized cell lines). Representative suitable cultured cell lines derived from humans and other mammals include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In some embodiments, the readout for an effect on the activity of the light regulated glutamate receptor is a direct measure of the activity of the light regulated glutamate receptor. A direct effect on the light regulated glutamate receptor is detected using an assay appropriate to the particular glutamate receptor. For example, where the light regulated glutamate receptor is an ion channel, the effect, if any, of the test agent on the activity of the ion channel is in some embodiments detected by detecting a change in the intracellular concentration of an ion. A change in the intracellular concentration of an ion can be detected using an indicator appropriate to the ion whose influx is controlled by the channel. For example, where the ion channel is a potassium ion channel, a potassium-detecting dye is used; where the ion channel is a calcium ion channel, a calcium-detecting dye is used; etc.

Suitable voltage-sensitive dyes include, but are not limited to, merocyanine-oxazolone dyes (e.g., NK2367); merocyanine-rhodanine dyes (e.g., NK2495, NK2761, NK2776, NK3224, and NK3225); oxonol dyes (e.g., RH155, RH479, RH482, RH1691, RH1692, and RH1838); styryl dyes (e.g., RH237, RH414, RH421, RH437, RH461, RH795, JPW1063, JPW3028, di-4-ANEPPS, di-9-ANEPPS, di-2-ANEPEQ, di-12-ANEPEQ, di-8-ANEPPQ, and di-12-ANEPPQ); and the like.

Suitable intracellular $K^+$ ion-detecting dyes include, but are not limited to, $K^+$-binding benzofuran isophthalate and the like.

Suitable intracellular $Ca^{2+}$ ion-detecting dyes include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, fura-4F, fura-5F, fura-6F, fluo-4, fluo-5F, fluo-5N, Oregon Green 488 BAPTA, Calcium Green, Calcein, Fura-C18, Calcium Green-C18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo-5F, Fluo-4FF, Mag-Fluo-4, Aequorin, dextran conjugates or any other derivatives of any of these dyes, and others (see, e.g., the catalog or Internet site for Molecular Probes, Eugene, see, also, Nuccitelli, ed., *Methods in Cell Biology, Volume* 40: *A Practical Guide to the Study of Calcium in Living Cells*, Academic Press (1994); Lambert, ed., *Calcium Signaling Protocols* (Methods in Molecular Biology Volume 114), Humana Press (1999); W. T. Mason, ed., *Fluorescent and Luminescent Probes for Biological Activity. A Practical Guide to Technology for Quantitative Real-Time Analysis*, Second Ed, Academic Press (1999); *Calcium Signaling Protocols* (Methods in Molecular Biology), 2005, D. G. Lamber, ed., Humana Press).

In particular embodiments of interest, a subject screening method is useful for identifying agents that alter the sense of taste. In other embodiments, a subject screening method is useful for identifying agents that affect one or more neurological functions of a mammalian subject. In other embodiments, a subject screening method is useful for identifying agents that are selective for a particular receptor type or subtype, where the screening method involves determining the effect of the agent on a first subtype and a second subtype, where an effect on the first subtype, and a reduced effect (or substantially no effect) on the second subtype indicates selectivity of the test agent for the first subtype.

Pharmaceutical Compositions

The present invention provides pharmaceutical compositions comprising a subject synthetic regulator. In some embodiments, the pharmaceutical composition is suitable for administering to an individual in need thereof.

A pharmaceutical composition comprising a subject synthetic regulator may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A pharmaceutical composition comprising a subject synthetic regulator can optionally include a pharmaceutically acceptable carrier(s) that facilitate processing of an active ingredient into pharmaceutically acceptable compositions. As used herein, the term "pharmacologically acceptable carrier" refers to any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in "Pharmaceutical Dosage Forms and Drug Delivery Systems" (Howard C. Ansel et al., eds., Lippincott Williams & Wilkins Publishers, $7^{th}$ ed. 1999); "Remington: The Science and Practice of Pharmacy" (Alfonso R. Gennaro ed., Lippincott, Williams & Wilkins, $20^{th}$ 2000); "Goodman & Gilman's The Pharmacological Basis of Therapeutics" Joel G. Hardman et al., eds., McGraw-Hill Professional, 10.sup.th ed. 2001); and "Handbook of Pharmaceutical Excipients" (Raymond C. Rowe et al., APhA Publications, $4^{th}$ edition 2003).

A subject pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a subject pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a subject pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A subject synthetic regulator can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public In the subject methods, a subject synthetic regulator may be administered to the host using any convenient means capable of resulting in the desired reduction in disease condition or symptom. Thus, a subject synthetic regulator can be incorporated into a variety of formulations for therapeutic administration. More particularly, a subject synthetic regulator can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

A subject synthetic regulator can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject synthetic regulator can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

A subject synthetic regulator can be utilized in aerosol formulation to be administered via inhalation. A subject synthetic regulator can be formulated into pressurized acceptable propellants such as dichlorodifluoromethane, propane, nitrogen and the like.

Furthermore, a subject synthetic regulator can be made into suppositories by mixing with a variety of bases such as emulsifying bases or water-soluble bases. A subject synthetic regulator can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject synthetic regulator in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject synthetic regulator calculated in an amount sufficient to produce the desired effect in association with a pharmaceutically acceptable diluent, carrier or vehicle. The specifications for a subject synthetic regulator depend on the particular compound employed and the effect to be achieved, and the pharmacodynamics associated with each compound in the host.

A subject synthetic regulator can be administered as injectables. Injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, a subject synthetic regulator is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Reversibly Caged Glutamate

Materials and Methods
Photostationary State Determination by NMR

Cis/trans photoisomerization of 2 was studied by $^1$H NMR, with in situ irradiation of the sample using a Polychrome V system monochromator (TILL Photonics) containing a 150 W Xenon short arc lamp with an output range of 320-680 nm. The half-power bandwidth was 14 nm. A 500 μl aliquot of a 100 mM sample in $D_2O$ was prepared in a screw-capped 528-TR-7 NMR tube (Wilmad). A FT-600-UMT fiber optic cable (NA 0.39) (Thorlabs) was coupled at one end to the monochromator using a custom fitting and the other end inserted into the NMR tube a few millimeters above the solution. Each sample was irradiated at the desired wavelength for 30 minutes to reach the photostationary state and 480 scans were required to obtain reasonable signal-to-noise ratios. The output from the fiber optic cable between 340-480 nm ranged from 0.3-9.0 μW/cm$^2$. Data were processed by isolating aromatic cis-trans $^1$H signals and summing their integrals to 1.0. All data were obtained in triplicate and averaged.

UV/Vis spectra

UV/Vis spectra were recorded on a Hewlett-Packard 8453 UV-Vis System. All solutions were made in the extracellular buffer for HEK293 cells (in mM): 135 NaCl, 5.4 KCl, 0.9 $MgCl_2$, 1.8 $CaCl_2$, and 10 HEPES at pH 7.6 (NaOH). Pure trans-2 was obtained by preparing a 50 μM solution in the dark and immediately taking a spectrum. Spectra at 380 and 500 nm were obtained by irradiating the sample at the designated wavelengths using a Polychrome V system monochromator (TILL Photonics) containing a 150 W Xenon short arc lamp with an output range of 320-680 nm until they reached a photostationary state. The spectrum of pure cis-2 was calculated as follows (see, e.g., Fischer, E. *J. Phys. Chem.* 1967, 71, 3704-3706):

$$D_{cis} = D_{trans} + \Delta/\alpha \quad (1)$$

where $D_{cis}$ and $D_{trans}$ denote the optical density of pure solutions of cis- and trans-2, Δ is the change in optical density between a pure trans solution and that at a given wavelength (λ) of irradiation ($\Delta = D_\lambda - D_{trans}$), and α is the photostationary state fraction of cis-2 at wavelength λ (obtained by NMR using the method above).

Rate of Isomerization in Bulk Solution

The rate of isomerization was calculated on a Hewlett Packard 8453 UV-Vis System monitoring absorbance at 360 nm over the course of 5 min (300 sec). A 1 mL aliquot of a 20 μM solution of pure trans-2 was placed in a 1 mL quartz cuvette with a path length of 1.0 cm. The solution was irradiated at a 90° angle from that of absorbance monitoring at 380 nm (power output: 3.36 mW at 380 nm) with a path length of irradiation of 2.5 cm. Absorbance was monitored every 5 sec and fit to a single exponential. Following irradiation at 380 nm the cuvette was then irradiated at 500 nm (power output: 3.82 mW at 500 nm) and monitored under similar conditions. All data were obtained in triplicate and averaged.

Half-Life of Thermal Relaxation

The half-life of thermal relaxation was calculated on a Genesys 6 Spectrophotometer (Thermo Electron Corporation), monitoring absorbance at 360 nm over the course of 12 hours, in 30 minute intervals. The data was well fit to a single exponential. Measurements were done in triplicate and averaged.

Cell Culture and Transfection

HEK293 cells were plated at approximately $3 \times 10^6$ cells/ml on poly-L-lysine-coated glass coverslips (Deutsche Spiegelglas, Carolina Biological) and maintained in DMEM with 5% newborn calf serum, 0.2 mg/ml streptomycin, and 200 U/ml penicillin at 37° C. Cells were transiently transfected with various plasmids using lipofectamine 2000 (Invitrogen). The amount of total transfected ionotropic glutamate receptor-2 (iGluR2), iGluR5, and iGluR6 DNA and enhanced yellow fluorescent protein (EYFP) fusion DNA per 0.5 mL well was fixed at 0.7 μg and 0.3 μg, respectively. All recordings were carried out 24 to 48 h after transfection.

Whole-Cell Patch Clamping

Patch clamp recordings were carried out using an Axopatch 200A amplifier in the whole cell mode. HEK cells were voltage clamped at −60 mV and hippocampal neurons were current clamped at −65 mV. Pipettes had resistances 2-6 MΩ. For experiments in HEK cells, pipettes were filled with a solution containing (in mM): 145 CsCl, 5 EGTA, 0.5 $CaCl_2$, 1.0 $MgCl_2$ and 10 HEPES at pH7.2 (CsOH). The extracellular solution contained (in mM): 135 NaCl, 5.4 KCl, 0.9 $MgCl_2$, 1.8 $CaCl_2$, and 10 HEPES at pH 7.6 (NaOH). Cells were preincubated for 10 min in control solution containing 300 mg/l Concanavalin A type VI (Sigma) in order to block desensitization. For experiments in hippocampal neurons, pipettes were filled with a solution containing (in mM): 10 NaCl, 1 EGTA, 135 K-gluconate, 2.0 $MgCl_2$, 10 HEPES and 2 Mg-ATP at pH7.4 (KOH). The extracellular solution contained (in mM): 138 NaCl, 1.5 KCl, 1.2 $MgCl_2$, 2.5 $CaCl_2$, 10 glucose and 10 HEPES at pH 7.3 (NaOH). L-Glutamate, DNQX, and compound 2 were applied as reported in text and figures with complete exchange of the bath solution occurring in less than 10 sec. Compound 2 was not pre-irradiated prior to perfusion, but the bath and coverslip were continuously under illumination as denoted in traces. Following complete exchange of the bath, perfusion of 2 was stopped prior to switching illumination wavelengths. Illumination was applied using a TILL Photonics Polychrome V monochromator through a 40×/0.60 W objective (power output: 4.8 mW/mm$^2$ at 500 nm and 1.8 mW/mm$^2$ at 380 nm, as measured with a Newport optical power meter). Data was recorded with pClamp software, which was also used to automatically control the monochromator by means of sequencing keys. The results are representative data from multiple cells in at least three independent cultures.

Synthesis

All non-aqueous reactions were performed using flame- or oven-dried glassware under an atmosphere of dry nitrogen. Commercial reagents were used as received. Non-aqueous reagents were transferred under nitrogen with a syringe or cannula. Solutions were concentrated in vacuo on a Buchi rotary evaporator. Diisopropylethylamine (DIPEA) was distilled from calcium hydride prior to use. Tetrahydrofuran (THF) and methylene chloride ($CH_2Cl_2$) were passed through a column of activated alumina under $N_2$-pressure prior to use. N,N-Dimethyl formamide (DMF) was degassed with a stream of $N_2$, dried over molecular sieves, and used without further purification. Chromatographic purification of products was accomplished using flash column chromatography on ICN 60 32-64 mesh silica gel 63 (normal phase) or Waters Preparative C18 125 Å 55-105 μm silica gel (reversed phase), as indicated. Thin layer chromatography (TLC) was performed on EM Reagents 0.25 mm silica gel 60-$F_{254}$ plates. Visualization of the developed chromatogram was performed using fluorescence quenching, $KMnO_4$, ceric ammonium molybdate (CAM), or iodine stains. IR spectra were measured with a Genesis FT-IR spectrometer by thin film or Avatar 370 FT-IR by attenuated total reflectance accessory. Optical rotations were measured using a Perkin-Elmer 241 Polarimeter at 25° C. and 589 nm. $^1$H and $^{13}$C NMR spectra were recorded in deuterated solvents on Bruker AVB-400, AVQ-400, or DRX-500 spectrometers and calibrated to the residual solvent peak. Multiplicities are abbreviated as follows: s=singlet, d=doublet, t=triplet, q=quartet, m=multiplet, app=apparent, br=broad.

Scheme S1: Synthesis of photochromic agonist 2.

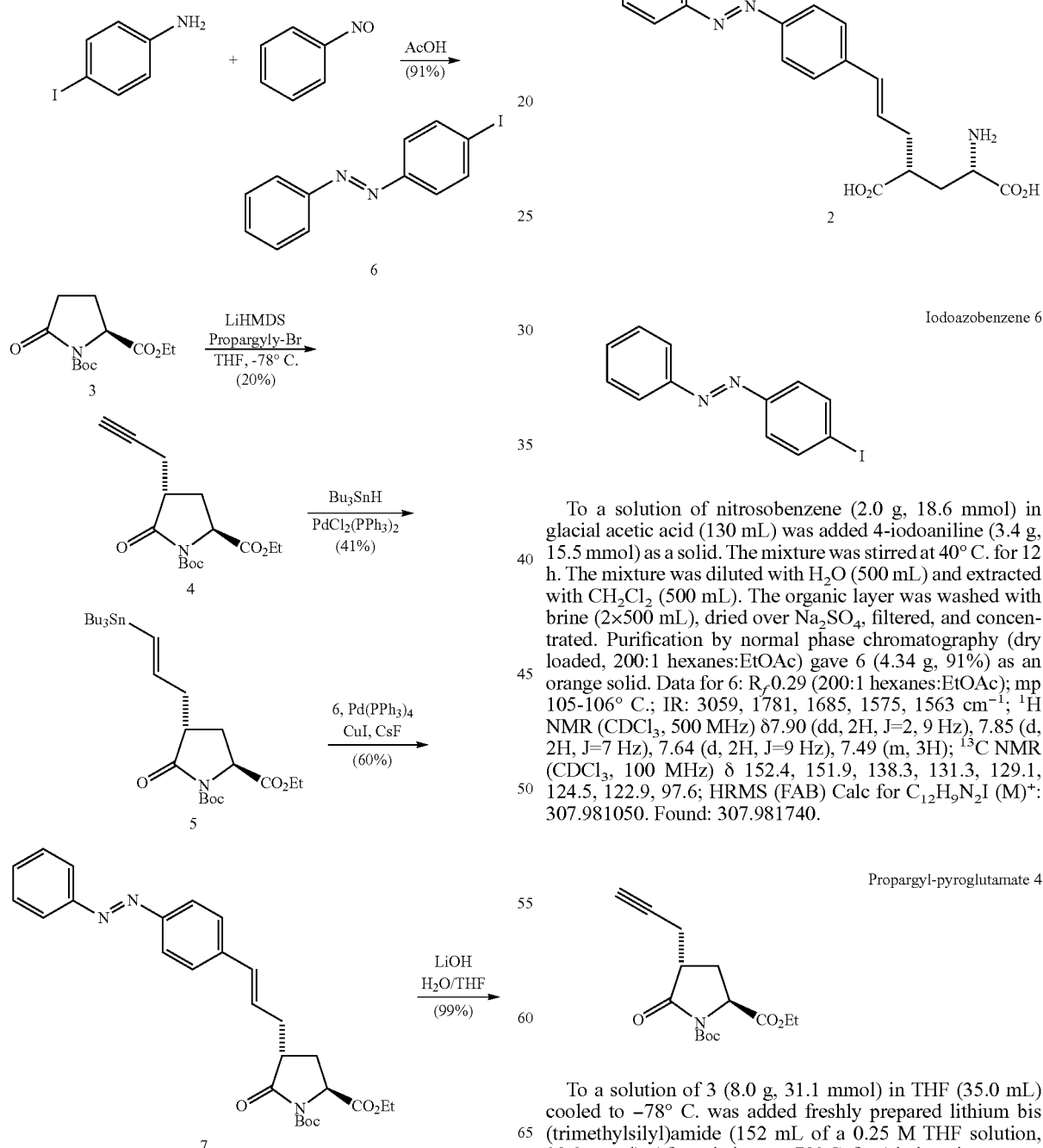

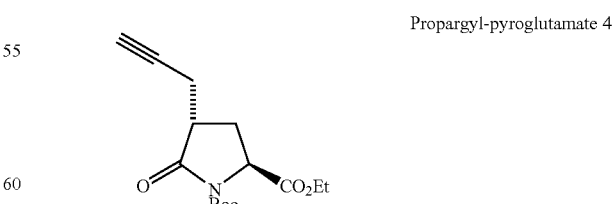

Iodoazobenzene 6

To a solution of nitrosobenzene (2.0 g, 18.6 mmol) in glacial acetic acid (130 mL) was added 4-iodoaniline (3.4 g, 15.5 mmol) as a solid. The mixture was stirred at 40° C. for 12 h. The mixture was diluted with $H_2O$ (500 mL) and extracted with $CH_2Cl_2$ (500 mL). The organic layer was washed with brine (2×500 mL), dried over $Na_2SO_4$, filtered, and concentrated. Purification by normal phase chromatography (dry loaded, 200:1 hexanes:EtOAc) gave 6 (4.34 g, 91%) as an orange solid. Data for 6: $R_f$ 0.29 (200:1 hexanes:EtOAc); mp 105-106° C.; IR: 3059, 1781, 1685, 1575, 1563 cm$^{-1}$; $^1$H NMR (CDCl$_3$, 500 MHz) δ7.90 (dd, 2H, J=2, 9 Hz), 7.85 (d, 2H, J=7 Hz), 7.64 (d, 2H, J=9 Hz), 7.49 (m, 3H); $^{13}$C NMR (CDCl$_3$, 100 MHz) δ 152.4, 151.9, 138.3, 131.3, 129.1, 124.5, 122.9, 97.6; HRMS (FAB) Calc for $C_{12}H_9N_2I$ (M)$^+$: 307.981050. Found: 307.981740.

Propargyl-pyroglutamate 4

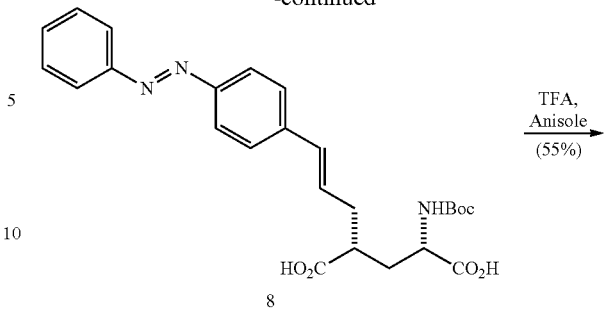

To a solution of 3 (8.0 g, 31.1 mmol) in THF (35.0 mL) cooled to −78° C. was added freshly prepared lithium bis (trimethylsilyl)amide (152 mL of a 0.25 M THF solution, 38.9 mmol). After stirring at −78° C. for 1 h the mixture was cannulated under nitrogen pressure into a solution of propargyl bromide (10.0 mL of a 80% solution in toluene, 89.6 mmol) also at −78° C. The resulting mixture was stirred at −78° C. for 2 h. The reaction mixture was quenched at −78° C. with a saturated ammonium chloride solution and then extracted with $CH_2Cl_2$ (800 mL). The organic layer was washed with brine (2×600 mL), dried over $Na_2SO_4$, filtered, and concentrated. Purification by normal phase chromatography (2:1→3:2 hexanes:$Et_2O$) gave 4 (1.85 g, 20%) as a clear oil. Data for 4: $R_f$ 0.21 (2:1 hexanes:$Et_2O$); $[\alpha]_D$=−36.3 (c 1.0, in $CHCl_3$); 379 nm; IR: 3271, 2981, 2936, 2910, 1793, 1745, 1720 $cm^{-1}$; $^1$H NMR ($CDCl_3$, 400 MHz) δ 4.59 (dd, 1H, J=2, 9 Hz), 4.24 (q, 2H, J=7 Hz), 2.85 (m, 1H), 2.66 (m, 1H), 2.48 (m, 1H), 2.30 (m, 2H), 2.00 (t, 2H, J=3 Hz), 1.50 (s, 9H), 1.29 (t, 3H, J=7 Hz); $^{13}$C NMR (MeOH-$d_4$, 125 MHz) δ 173.0, 171.0, 149.2, 83.6, 80.0, 70.7, 61.7, 56.9, 40.6, 27.8, 27.3, 19.2, 14.1; HRMS (FAB) Calc for $C_{15}H_{22}N_1O_5$ $(MH^+)^+$: 296.149798. Found: 296.149090.

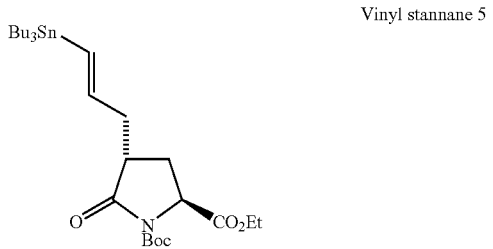

Vinyl stannane 5

To a solution of 4 (2.93 g, 9.92 mmol) and $PdCl_2(PPh_3)_2$ (13.9 mg, 0.0198 mmol) in THF (29.0 mL) at 0° C. was added tributyltin hydride (2.89 mL, 10.91 mmol) dropwise over 30 min. After stirring for 10 min at room temperature, the mixture was concentrated and purified by normal phase chromatography (20:1→92:8 hexanes:EtOAc) to yield 5 (2.36 g, 41%) as a clear oil. Data for 5: $R_f$ 0.26 (9:1 hexanes:EtOAc); $[\alpha]_D$=−31.2 (c 1.0, in $CHCl_3$); IR: 2956, 2926, 2871, 2851, 1795, 1750, 1720, 1599 $cm^{-1}$; $^1$H NMR ($CDCl_3$, 500 MHz) δ 5.85 (m, 1H), 5.83 (m, 1H), 4.52 (dd, 1H, J=2, 10 Hz), 4.22 (q, 2H, J=7 Hz), 2.72 (m, 2H), 2.24 (m, 1H), 2.13 (ddd, 1H, J=2, 9 Hz), 2.01 (m, 1H), 1.49 (s, 9H), 1.46 (m, 6H), 1.28 (m, 9H), 0.87 (m, 15H); $^{13}$C NMR (DMSO-$d_6$, 100 MHz) δ 174.6, 171.4, 149.5, 144.4, 132.0, 83.5, 61.6, 57.2, 41.2, 38.6, 29.1, 27.9, 27.5, 27.2, 14.2, 13.7, 9.6 $cm^{-1}$; LRMS (FAB) Calc for $C_{23}H_{40}NO_5Sn$ $(M-C_4H_9)^+$: 530. Found: 530.

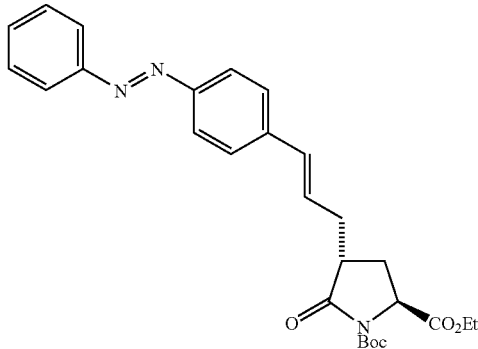

Azobenzene pyroglutamate 7

A mixture of 5 (636 mg, 1.08 mmol), 6 (257 mg, 0.833 mmol), $Pd(PPh_3)_4$ (48 mg, 0.042 mmol), CuI (16 mg, 0.083 mmol) and CsF (253 mg, 1.67 mmol) in DMF (25.0 mL) was heated to 65° C. for 8 h. The reaction mixture was diluted with $H_2O$ (400 mL) and extracted with EtOAc (2×250 mL). The organic layer was washed with brine (2×250 mL), dried, filtered and concentrated. Purification by normal phase chromatography (100:0→95:5 $CH_2Cl_2$:$Et_2O$) gave 7 (366 mg, 92%) as an orange solid. Data for 7: $R_f$ 0.29 (4:1 hexanes:EtOAc); mp 107-109° C.; $[\alpha]_D$=−25.0 (c 0.1, in $CHCl_3$); IR: 2979, 2934, 2445, 2392, 2294, 1789, 1747, 1717, 1597 $cm^{-1}$; $^1$H NMR ($CDCl_3$, 400 MHz) δ 7.90 (m, 4H), 7.49 (m, 5H), 6.52 (d, 1H, J=16 Hz), 6.27 (m, 1H), 4.57 (dd, 1H, J=2, 10 Hz), 4.24 (q, 2H, J=7 Hz), 2.83 (m, 2H), 2.44 (m, 1H), 2.24 (dd, 1H, J=2, 9 Hz), 2.09 (m, 1H), 1.51 (s, 9H), 1.29 (t, 3H, J=7 Hz); $^{13}$C NMR ($CDCl_3$, 100 MHz) δ 174.2, 171.2, 152.7, 151.7, 149.4, 139.6, 132.3, 130.9, 129.0, 127.9, 126.8, 123.2, 122.8, 83.6, 61.7, 57.1, 41.5, 33.7, 27.9, 27.8, 14.2; HRMS (FAB) Calc for $C_{27}H_{32}N_3O_5$ $(MH^+)^+$: 478.234197. Found: 478.234810.

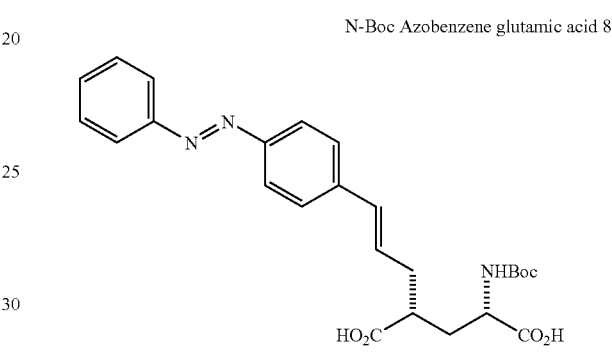

N-Boc Azobenzene glutamic acid 8

To a solution of 7 (224 mg, 0.469 mmol) in THF (25.0 mL) was added a 1.0 M aqueous solution of LiOH (25.0 mL). The mixture was stirred at room temperature for 2 h and then acidified to pH 2 with a 1.0 M HCl solution and extracted with EtOAc (3×20 mL). The combined organic layers were dried over $Na_2SO_4$, filtered, and concentrated. Purification by normal phase chromatography (94:4:2 $CH_2Cl_2$:MeOH:AcOH) gave 8 (216 mg, 99%) as an orange solid. Data for 8: $R_f$ 0.24 (94:4:2 $CH_2Cl_2$:MeOH:AcOH); mp 97-99° C.; $[\alpha]_D$=+12.0 (c 0.1, in $CHCl_3$); IR: 3412, 3321, 2979, 2925, 2385, 2348, 2297, 1710, 1512, 1501 $cm^{-1}$; $^1$H NMR (MeOH-$d_4$, 500 MHz) δ 7.88 (d, 2H, J=8 Hz), 7.85 (d, 2H, J=8 Hz), 7.50 (m, 5H), 6.56 (d, 1H, J=16 Hz), 6.37 (m, 1H), 4.17 (m, 1H), 2.71 (m, 1H), 2.58 (m, 1H), 2.51 (m, 1H), 2.24 (m, 1H), 1.80 (m, 1H), 1.44 (s, 9H); $^{13}$C NMR (DMSO-$d_6$, 125 MHz) δ 179.7, 177.5, 155.7, 152.6, 151.6, 139.7, 132.3, 130.8, 129.0, 127.8, 126.9, 123.2, 122.8, 80.7, 52.1, 41.8, 36.0, 31.5, 28.2; LRMS (ESI)$^-$ Calc for $C_{25}H_{28}N_3O_6$ $(M-H)^-$: 466.2. Found: 466.3.

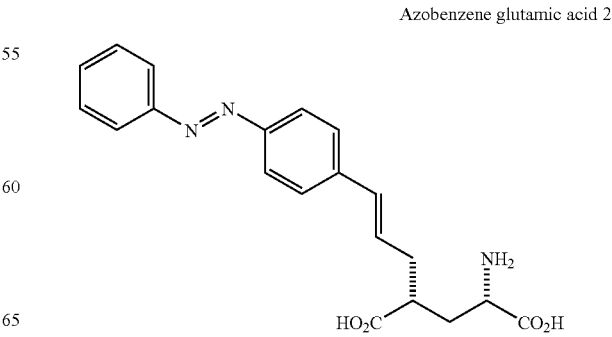

Azobenzene glutamic acid 2

To a solution of 8 (160 mg, 0.342 mmol) and anisole (1.1 mL, 10.1 mmol) in $CH_2Cl_2$ (11.0 mL) was added TFA (6.0 mL) dropwise at room temperature. The mixture was stirred at room temperature for 1 h, diluted with diethyl ether (100 mL), and the resulting precipitate was filtered and discarded. The filtrate was concentrated and subsequently redissolved in a minimal amount of saturated $NaHCO_3$ solution and acetonitrile. Purification by reversed phase chromatography (100:0→85:15 $H_2O$:MeCN) gave 2 (69 mg, 55%) as the monosodium, di-hydrate salt. Data for 2: mp>170° C. (dec); $[\alpha]_D$=+45.0 (c 0.1, in DMSO); IR: 2921, 1690, 1596 $cm^{-1}$; $^1H$ NMR (MeOH-$d_4$, 500 MHz) δ 7.88 (d, 2H, J=8 Hz), 7.83 (d, 2H, J=8 Hz), 7.52 (m, 5H), 6.56 (d, 1H, J=16 Hz), 6.47 (m, 1H), 3.68 (m, 1H), 2.64 (m, 1H), 2.58 (m, 1H), 2.48 (m, 1H), 2.19 (m, 1H), 2.02 (m, 1H); $^{13}C$ NMR (MeOH-$d_4$, 125 MHz) δ 182.8, 174.9, 154.1, 152.8, 142.4, 132.2, 132.1, 132.0, 130.2, 127.9, 124.1, 123.7, 54.5, 46.2, 37.8, 33.8; LRMS (ESI)$^-$ Calc for $C_{20}H_{20}N_3O_4$ (M-H)$^-$: 366.1. Found: 366.1. Anal. Calculated for $C_{20}H_{24}N_3NaO_6$ (M-H+Na+$2H_2O$): C, 56.47%; H, 5.69%; N, 9.88%. Found: C, 56.25%, H, 5.48%; N, 8.51%.

Results

The possibility of a non-tethered photochromic agonist that could function at wild-type receptors was investigated. The design was based upon the report of a series of (2S,4R)-4-substituted glutamate analogues that are potent and selective iGluR5 and 6 kainate receptor (KAR) agonists. Pedregal et al. (2000). *J. Med. Chem.* 43:1958-196. In particular, the napthyl group of LY339434 (1) was replaced with an azobenzene to generate compound 2 (Scheme 1). It was envisioned that the change in shape and polarity between trans-2 and cis-2 would generate differences in affinity to the receptor ligand binding domains.

The stereoselective synthesis of 2 was achieved starting from N-Boc protected ethyl pyroglutamate 3 (Scheme 2).

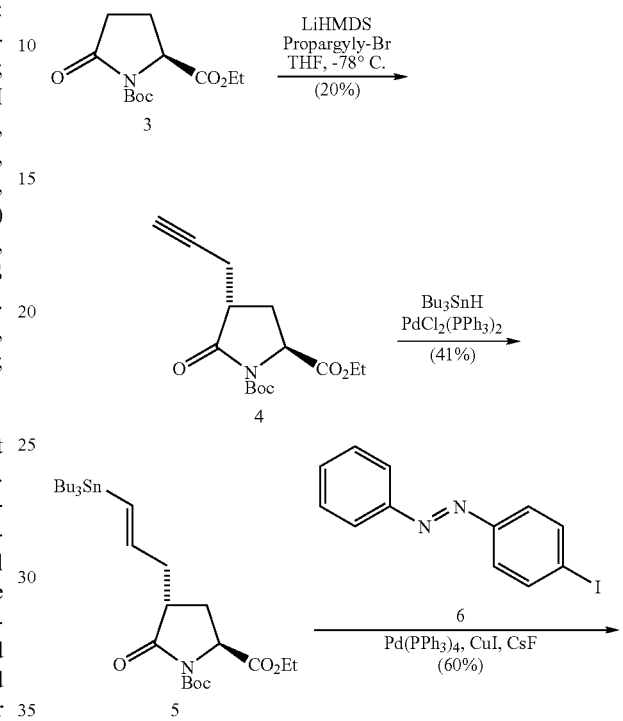

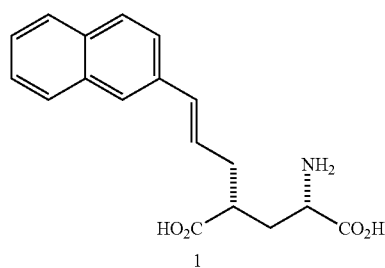

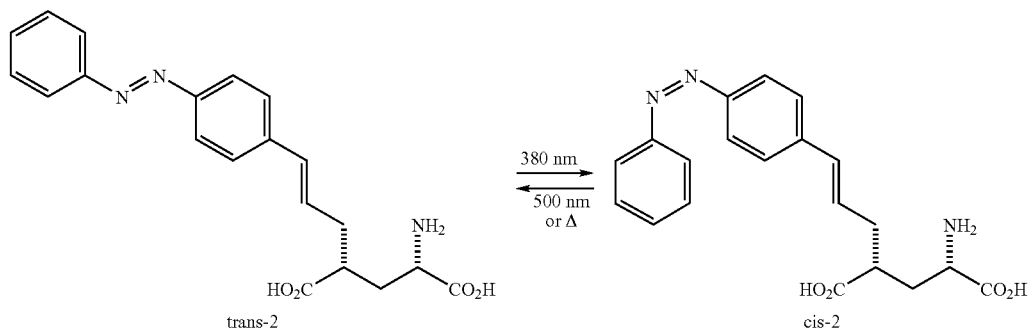

-continued

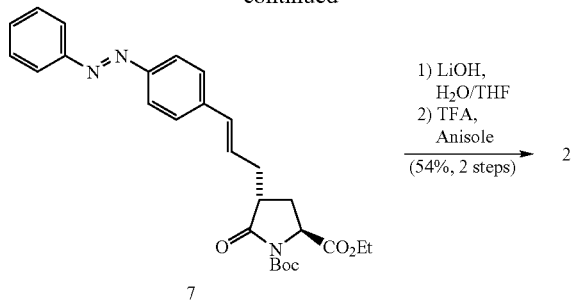

1) LiOH, H₂O/THF
2) TFA, Anisole
(54%, 2 steps) → 2

Diastereoselective alkylation of 3 with propargyl bromide gave alkyne 4, which underwent hydrostannation to afford vinyl stannane 5. Palladium catalyzed Stille-coupling with iodoazobenzene 6, obtained by the condensation of 4-iodoaniline with nitrosobenzene then gave the N-Boc protected azobenzene-pyroglutamate 7. Finally, deprotection of 7 yielded 2 as the dihydrate, mono-sodium salt.

NMR experiments with in situ illumination of the sample revealed photostationary states containing 76.3±0.3% cis-2 at 380 nm and 89±1% trans-2 at 500 nm (mean±s.e.m., n=3).[13] Furthermore, the half-life of thermal relaxation from cis- to trans-2 in the dark was measured at 18±3 hrs (mean±s.e.m., n=3).

Compound 2 was assayed with whole-cell voltage clamp recordings in HEK293 cells transiently expressing wild-type iGluR6(Q) and pretreated with 0.3 mg/mL concanavalin A (ConA) to block desensitization. Channel activation depended on the wavelength of irradiation, displaying increased inward currents in the trans-relative to the cis-state (FIG. 1). Activity was competitively blocked by the non-NMDA receptor antagonist DNQX.

FIG. 1. Whole cell voltage clamp recording of iGluR6(Q) currents in HEK293 cells under UV-visible illumination.

To investigate the cis/trans-agonist profile of 2, dose-response curves were generated with iGluR5(Q) and iGluR6(Q) under both 380 and 500 nm light (FIG. 2). In agreement with previous reports of (2S,4R)-4-glutamic acid analogues, 2 demonstrated high selectivity at iGluR5 over iGluR6 receptors, with approximately half-maximal efficacy with respect to a 300 μM glutamate evoked response. The apparent agonist affinity ($EC_{50}$) of iGluR5 was 9 μM under 500 nm illumination and reduced ~10-fold under 380 nm light. Due to the solubility constraints of 2, full titration curves at iGluR6 could not be generated. The AMPA receptor iGluR2 failed to produce inward currents in the presence of 250 μM 2, demonstrating the subtype selectivity of this agonist.

FIG. 2. Dose-response curves for inward currents evoked by 2 at iGluR5 and iGluR6 expressing HEK293 cells under 380 and 500 nm illumination.

Activation and deactivation proceeded at rates ($\tau_{on-500nm}$=310±15 ms; $\tau_{off-380nm}$=250±14 ms; mean±s.e.m., n=3) slower than the microsecond timescale of traditional uncaging experiments. However, these studies were conducted at light intensities (4.8 mW/mm² at 500 nm and 1.8 mW/mm² at 380 nm) several orders of magnitude weaker than laser pulse-photolysis techniques. Much faster rates of isomerization are expected at comparable light intensities.

Figure 3:
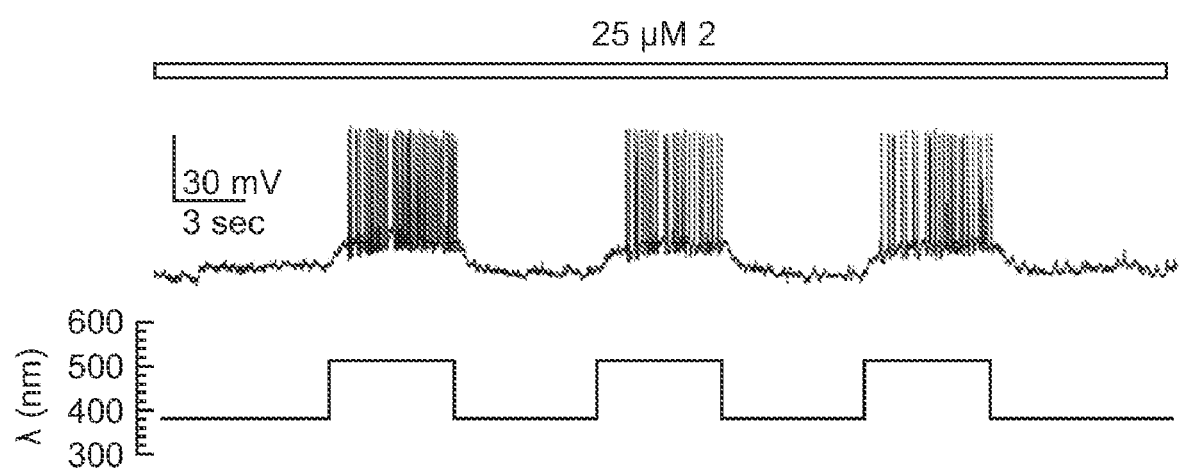
FIG. 3 depicts whole-cell current clamp recording of cultured rat hippocampal neurons in the presence of 25 µm 2 under 380 nm and 500 nm illumination.

The ability of 2 to depolarize cultured rat hippocampal neurons, which are known to express the KAR subunits iGluR6 and KA2, but not iGluR5, was tested. Neurons were exposed to a 25 μM concentration of 2 under 380 nm light and current clamped at −65 mV, without pretreatment with ConA. Switching wavelengths between 380 and 500 nm light was then sufficient to trigger, and extinguish, sustained trains of action potentials (FIG. 3). While iGluR6 channels are only activated to a small extent at 25 μM (FIG. 2), this can still produce significant depolarization. Given the large number of receptors in the cell, only a small fraction needs to be concurrently activated by glutamate release to trigger neuronal firing.

FIG. 3. Whole cell current clamp recording of cultured rat hippocampal neurons in the presence of 25 μM 2 under 380 and 500 nm illumination.

Figure 4A:
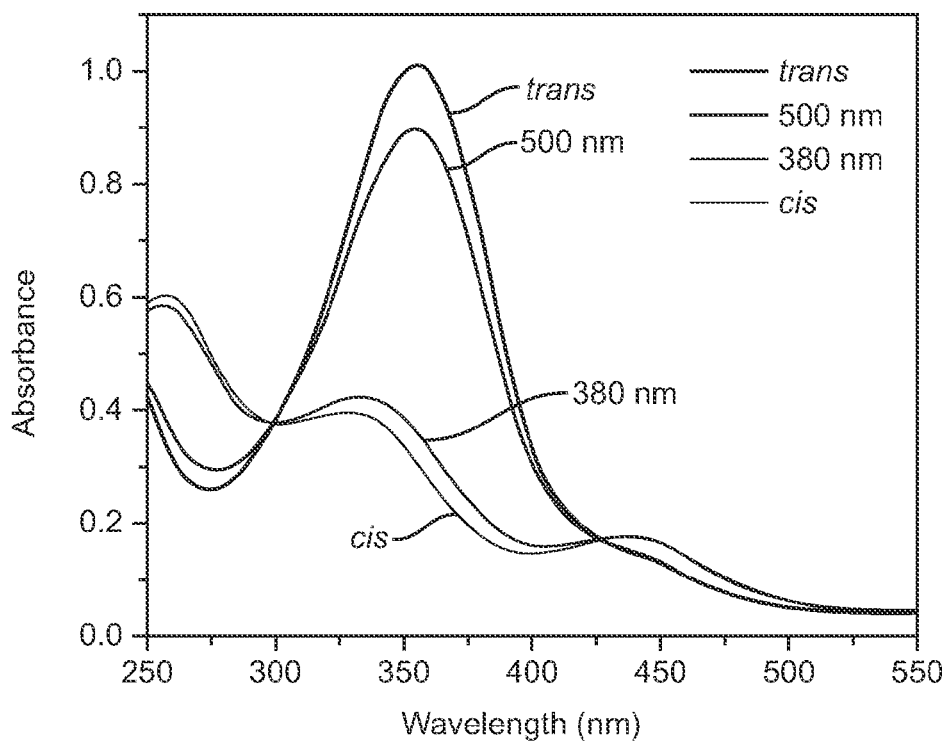
FIG. 4A depicts UV/Vis spectra of 50 µM 2 in the pure trans-state, under 380 and 500 nm irradiation, and extrapolated pure cis-state.
Figure 4B:
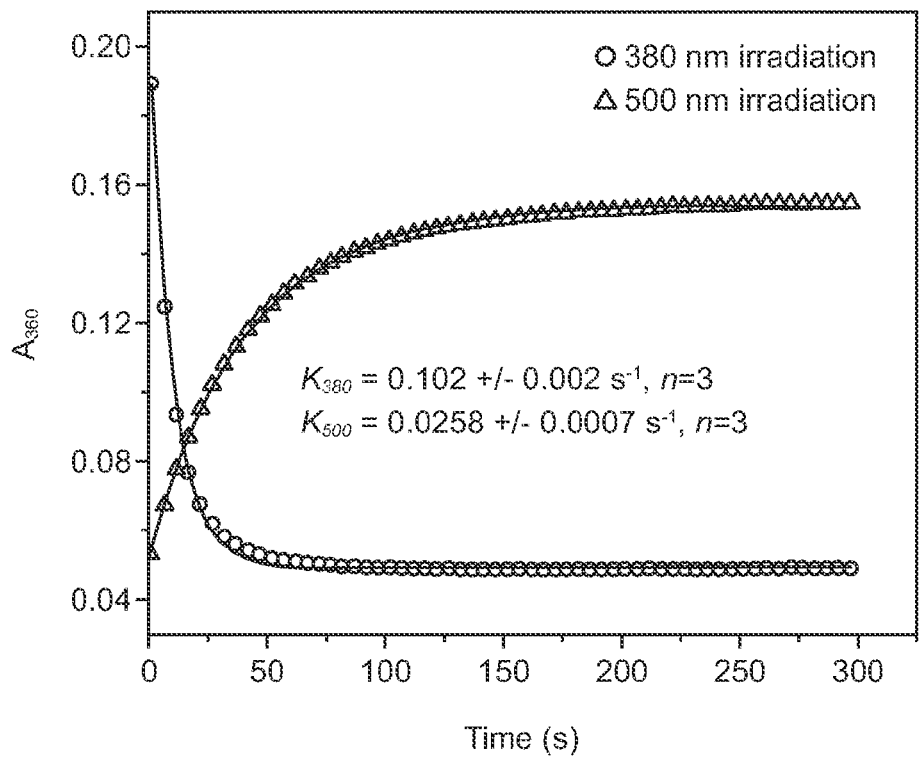
FIG. 4B depicts rates of trans→cis (under 380 nm irradiation) and cis→trans (under 500 nm irradiation) isomerization of 2 as monitored by absorbance at 360 nm.

FIGS. 4A and 4B. (A) UV/Vis spectra of 50 μM 2 in the pure trans-state, under 380 and 500 nm irradiation, and extrapolated pure cis-state. (B) Rates of trans→cis (under 380 nm irradiation) and cis→trans (under 500 nm irradiation) isomerization of 2 as monitored by absorbance at 360 nm.

Figure 5A:
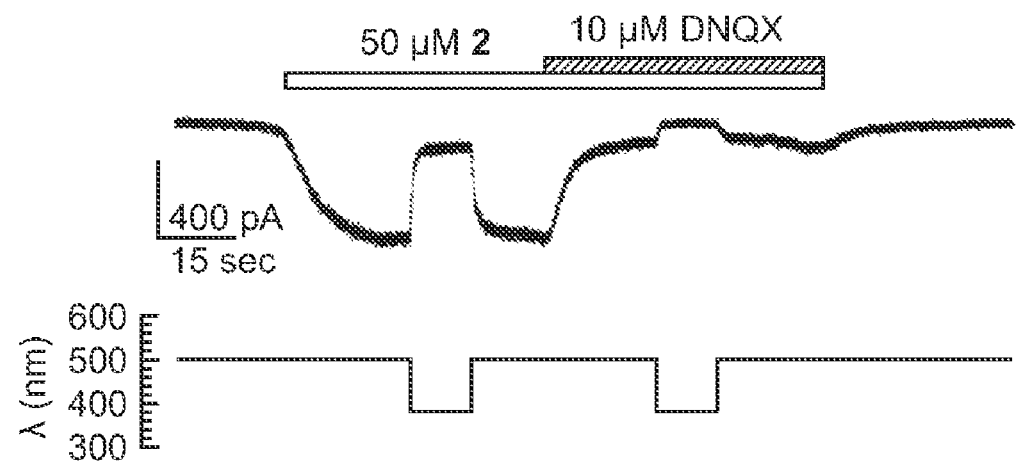
FIGS. 5A and 5B depict pharmacological block of light activation with 2 by the non N-methyl-D-aspartate (NMDA) glutamate receptor antagonist (6,7-dinitroquinoxaline-2,3-dione) (DNQX).
Figure 5B:
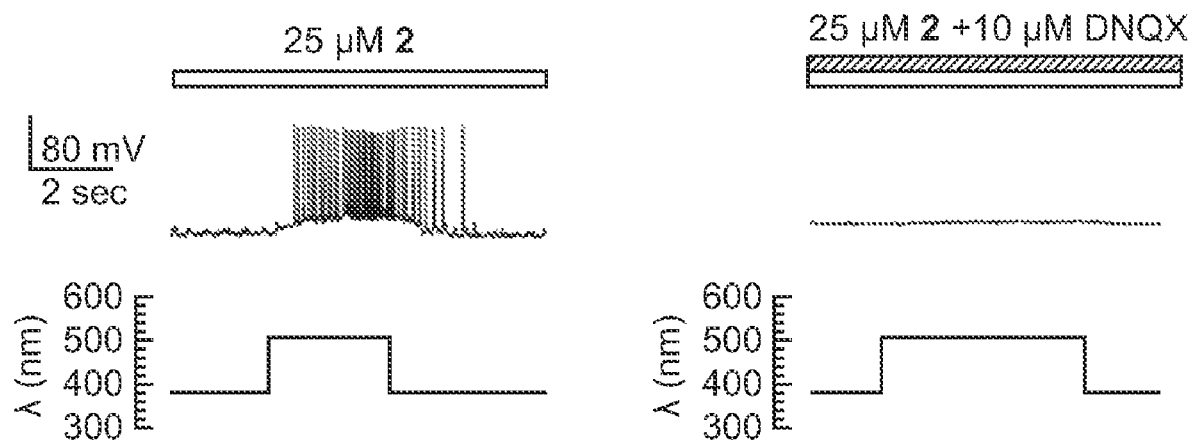

FIGS. 5A and 5B. Pharmacological block of light activation with 2 by the non-NMDA glutamate receptor antagonist DNQX. (A) Whole cell voltage clamp recording from HEK293 cells expressing iGluR6(Q) in the presence of 50 μM 2 alone and together with 10 μM DNQX under 380 and 500 nm illumination. (B) Whole cell current clamp recording from cultured rat hippocampal neurons in the presence of 25 μM 2 alone and together with 10 μM DNQX under 380 and 500 nm illumination (same cell).

Figure 6:
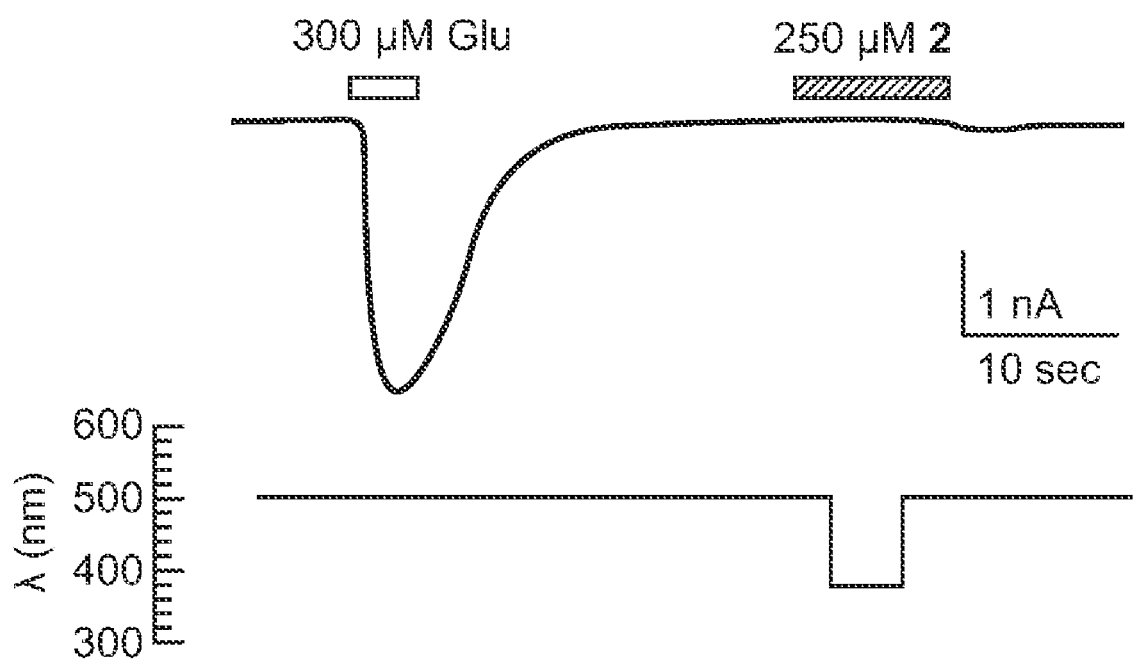
FIG. 6 depicts whole cell voltage clamp recordings from HEK293 cells expressing the non-desensitizing mutant iGluR2(Q)flip-L483Y under 380 and 500 nm illumination.

FIG. 6. Whole cell voltage clamp recordings from HEK293 cells expressing the non-desensitizing mutant iGluR2(Q)flip-L483Y under 380 and 500 nm illumination. Although 300 μM Glu evokes a large inward current, 250 μM 2 has no effect in either the trans- (500 nm) or cis-state (380 nm).

Taken together, these results describe a simple approach for obtaining remote control of iGluR activity and neuronal firing with a photochromic agonist. The active agonist is subtype-specific, possesses good efficacy and affinity, and can be conveniently controlled by the wavelength of light used.

REFERENCES

1. Gillespie, D. C., et al. In *Dynamic Studies in Biology*, First Edition; Goeldner, M., Givens, R., Eds.; Wiley VCH, Weinheim, 2005; 232-251.
2. Callaway, E. M.; Yuste, R. *Curr. Opin. Neurobiol.* 2002, 12, (5), 587-592.
3. Hess, G. P. In *Dynamic Studies in Biology*, First Edition; Goeldner, M., Givens, R., Eds.; Wiley VCH, Weinheim, 2005; 232-251.
4. Mayer, M. L. *Nature* 2006, 440, (7083), 456-462.
5. Kaufman, H.; Vratsanos, S. M.; Erlanger, B. F. *Science* 1968, 162, (861), 1487-1489.
6. Bartels, E.; Wasserman, N. H.; Erlanger, B. F. *Proc. Natl. Acad. Sci. U.S.A.* 1971, 68, (8), 1820-1823.
7. Fujita, D.; Murai, M.; Nishioka, T.; Miyoshi, H. *Biochemistry* 2006, 45, (21), 6581-6586.
8. Caamano, A. M.; Vazquez, M. E.; Martinez-Costas, J.; Castedo, L.; Mascarenas, J. L. *Angew. Chem., Int. Ed. Engl.* 2000, 39, (17), 3104-3107.
9. Mayer, G.; Heckel, A. *Angew. Chem., Int. Ed. Engl.* 2006, 45, (30), 4900-4921.
10. Givens, R. S.; Weber, J. F. W.; Jung, A. H.; Park, C. In *Methods n Enzymology*, Marriott, G., Ed. Academic Press, New York, 1998, 291, 1-29.
11. Volgraf, M.; Gorostiza, P.; Numano, R.; Kramer, R. H.; Isacoff, E. Y.; Trauner, D. *Nature Chem. Biol.* 2006, 2, (1), 47-52.
12. Pedregal, C.; Collado, I.; Escribano, A.; Ezquerra, J.; Dominguez, C.; Mateo, A. I.; Rubio, A.; Baker, S. R.;

Goldsworthy, J.; Kamboj, R. K.; Ballyk, B. A.; Hoo, K.; Bleakman, D. *J. Med. Chem.* 2000, 43, (10), 1958-1968.
13. Tait, K. M.; Parkinson, J. A.; Bates, S. P.; Ebenezer, W. J.; Jones, A. C. *J. Photochem. Photobio. A* 2003, 154, (2-3), 179-188.
14. Kohler, M.; Burnashev, N.; Sakmann, B.; Seeburg, P. H. Neuron 1993, 10, (3), 491-500.
15. Partin, K. M.; Patneau, D. K.; Winters, C. A.; Mayer, M. L.; Buonanno, A. Neuron 1993, 11, (6), 1069-1082.
16. Honore, T.; Davies, S. N.; Drejer, J.; Fletcher, E. J.; Jacobsen, P.; Lodge, D.; Nielsen, F. E. *Science* 1988, 241 (4866), 701-703.
17. Ramesh, D.; Wieboldt, L. N.; Carpenter, B. K.; Hess, G. P. *Proc. Natl. Acad. Sci. U.S.A.* 1993, 90, (23), 11074-11078.
18. Chen. E.; Kumita, J. R.; Woolley, G. A.; Kliger, D. S. *J. Am. Chem. Soc.* 2003, 125, 12443-12449.
19. Janssens, N.; Lesage, A. S. J. *J. Neurochem.* 2001, 77, (6), 1457-1474.
20. Banghart, M.; Borges, K.; Isacoff, E. Y.; Trauner, D.; Kramer, R. H. *Nat. Neurosci.* 2004, 7, (12), 1381-1386.
21. Boyden, E. S.; Zhang, F.; Bamberg, E.; Nagel, G.; Deisseroth, K. *Nat. Neurosci.* 2005, 8, (9), 1263-1268.
22. Lima, S. Q.; Miesenbock, G. *Cell* 2005, 121, (1), 141-152

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A synthetic regulator of glutamate receptor function, the regulator comprising:
   a) a photoisomerizable group selected from an azobenzene, a fulgide, a spiropyran, a triphenyl methane, a thioindigo, a diarylethene, and an overcrowded alkene;
   b) a ligand that binds to a ligand binding site of said glutamate receptor, wherein the ligand is selected from the group consisting of glutamate, methylglutamate, 4-allyl glutamate, N-methyl-D-aspartate, D-serine, or glycine,
   wherein the ligand is covalently linked to the photoisomerizable group, and
   wherein the synthetic regulator does not comprise a linker domain comprising a binding moiety that provides for stable association with the glutamate receptor.
2. The synthetic regulator of claim 1, wherein the photoisomerizable group comprises an azobenzene.
3. The synthetic regulator of claim 1, wherein photoisomerization of the photoisomerizable group results in a change in the binding of the ligand to the ligand-binding site, thereby regulating the function of said glutamate receptor.
4. The synthetic regulator of claim 1, wherein the glutamate receptor is an ionotropic glutamate receptor.
5. The synthetic regulator of claim 4, wherein the ionotropic glutamate receptor is an N-methyl-D-aspartate (NMDA) receptor, an α-amino-3-hydroxy-5-methyl-4-isoxazole-propionate (AMPA) receptor, or a kainate (KA) receptor.
6. The synthetic regulator of claim 1, wherein the synthetic regulator has the structure:

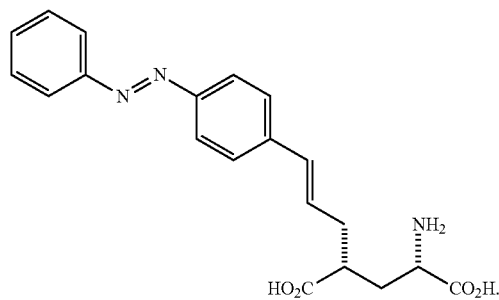

7. A pharmaceutical composition comprising:
a) the synthetic regulator of claim 1; and
b) a pharmaceutically acceptable excipient.

* * * * *